United States Patent
Arikawa et al.

(10) Patent No.: US 10,072,255 B2
(45) Date of Patent: Sep. 11, 2018

(54) MICROORGANISM HAVING REGULATED EXPRESSION OF (R)-SPECIFIC ENOYL-COA HYDRATASE GENE AND METHOD FOR PRODUCING POLYHYDROXYALKANOATE COPOLYMER USING SAME

(71) Applicant: KANEKA CORPORATION, Osaka-shi (JP)

(72) Inventors: Hisashi Arikawa, Hyogo (JP); Shunsuke Sato, Hyogo (JP); Keiji Matsumoto, Hyogo (JP)

(73) Assignee: KANEKA CORPORATION, Osaka-shi (JP)

( * ) Notice: Subject to any disclaimer, the term of this patent is extended or adjusted under 35 U.S.C. 154(b) by 0 days.

(21) Appl. No.: 15/115,394

(22) PCT Filed: Jan. 30, 2015

(86) PCT No.: PCT/JP2015/052758
§ 371 (c)(1),
(2) Date: Jul. 29, 2016

(87) PCT Pub. No.: WO2015/115619
PCT Pub. Date: Aug. 6, 2015

(65) Prior Publication Data
US 2017/0009221 A1    Jan. 12, 2017

(30) Foreign Application Priority Data

Jan. 31, 2014 (JP) .................... 2014-017873
Jan. 31, 2014 (JP) .................... 2014-017879

(51) Int. Cl.
*C12P 7/62* (2006.01)
*C12N 9/88* (2006.01)
*C12N 15/74* (2006.01)

(52) U.S. Cl.
CPC ............. *C12N 9/88* (2013.01); *C12N 15/74* (2013.01); *C12P 7/625* (2013.01); *C12Y 402/01017* (2013.01); *C12Y 402/01074* (2013.01)

(58) Field of Classification Search
None
See application file for complete search history.

(56) References Cited

U.S. PATENT DOCUMENTS

| | | | |
|---|---|---|---|
| 2003/0228669 A1 | 12/2003 | Huisman et al. | |
| 2011/0046339 A1* | 2/2011 | Park | C08G 63/06 528/361 |
| 2011/0091948 A1* | 4/2011 | Murakami | C12N 9/0006 435/148 |
| 2011/0144377 A1* | 6/2011 | Eliot | C12N 9/0006 560/190 |
| 2013/0071892 A1 | 3/2013 | Fukui et al. | |
| 2014/0073022 A1* | 3/2014 | Pfleger | C12P 7/62 435/135 |
| 2014/0234901 A1 | 8/2014 | Matsuda et al. | |
| 2014/0288009 A1 | 9/2014 | Sutherland et al. | |
| 2014/0349353 A1* | 11/2014 | Nomura | C12Y 402/0101 435/135 |
| 2016/0040197 A1 | 2/2016 | Fukui et al. | |

FOREIGN PATENT DOCUMENTS

| | | |
|---|---|---|
| EP | 0 052 460 A1 | 5/1982 |
| EP | 0 114 086 A2 | 7/1984 |
| EP | 0 533 144 A2 | 3/1993 |
| EP | 0 824 148 A2 | 2/1998 |
| EP | 2 540 835 A1 | 1/2013 |
| JP | 57-150393 A | 9/1982 |
| JP | 59-220192 A | 12/1984 |
| JP | 5-93049 A | 4/1993 |
| JP | 7-265065 A | 10/1995 |
| JP | 10-108682 A | 4/1998 |
| JP | 2001-340078 A | 12/2001 |
| JP | 2002-523050 A | 7/2002 |
| WO | 00/11188 A1 | 3/2000 |
| WO | 2008/090873 A1 | 7/2008 |
| WO | 2011/105379 A1 | 9/2011 |
| WO | 95/21257 A1 | 5/2013 |
| WO | 2013/065772 A1 | 5/2013 |
| WO | 2013/071356 A1 | 5/2013 |
| WO | 2014/133088 A1 | 9/2014 |

OTHER PUBLICATIONS

Yoshiharu Doi, et al., "Microbial Synthesis and Characterization of Poly(3-hydroxybutyrate-co-3-hydroxyhexanoate)," Macromolecules, vol. 28, No. 14, 1995, pp. 4822-4828.

Toshiaki Fukui, et al., "Cloning and Analysis of the Poly(3-Hydroxybutyrate-co-3-Hydroxyhexanoate) Biosynthesis Genes of Aeromonas caviae," Journal of Bacteriology, vol. 179, No. 15, Aug. 1997, pp. 4821-4830.

Yui Kawashima, et al., "Characterization and Functional Analyses of R-Specific Enoyl Coenzyme A Hydratases in Polyhydroxyalkanoate-Producing Ralstonia eutropha," Applied and Environmental Microbiology, vol. 78, No. 2, Jan. 2012, pp. 493-502.

International Search Report dated Apr. 21, 2015 in PCT/JP2015/052758 filed Jan. 30, 2015.

Partial Supplementary Search Report dated Jul. 25, 2017 in European Patent Application No. 15742617.2.

* cited by examiner

*Primary Examiner* — Richard C Ekstrom
(74) *Attorney, Agent, or Firm* — Oblon, McClelland, Maier & Neustadt, L.L.P.

(57) ABSTRACT

This invention relates to a microorganism that produces a polyhydroxyalkanoate (PHA) copolymer with a regulated monomer composition ratio and comprises a (R)-specific enoyl-CoA hydratase gene in the genome DNA, wherein a nucleotide sequence upstream of the (R)-specific enoyl-CoA hydratase gene comprises a modification consisting of a substitution(s), a deletion(s), an insertion(s), and/or an addition(s) of one or a plurality of nucleotides so that the expression of the (R)-specific enoyl-CoA hydratase gene is regulated, and to a method for producing a PHA copolymer using the microorganism.

16 Claims, No Drawings
Specification includes a Sequence Listing.

MICROORGANISM HAVING REGULATED EXPRESSION OF (R)-SPECIFIC ENOYL-COA HYDRATASE GENE AND METHOD FOR PRODUCING POLYHYDROXYALKANOATE COPOLYMER USING SAME

TECHNICAL FIELD

The present invention relates to a recombinant microorganism in which (R)-specific enoyl-CoA hydratase gene expression is regulated and to a method for producing a polyhydroxyalkanoate copolymer with regulated monomer composition ratio using the microorganism.

BACKGROUND ART

A polyhydroxyalkanoate (hereinafter, occasionally referred to as a "PHA") is a polyester-type organic polymer molecule produced by a variety of microorganisms. PHAs are biodegradable thermoplastic polymers and are also producible from renewable resources. Accordingly, some attempts have been made to industrially produce a PHA as an environmentally friendly material or biocompatible material for various industrial applications.

Currently, many microorganisms are known to accumulate PHAs as energy-storage substances therein. A representative example of a PHA is poly-3-hydroxybutyric acid (hereinafter, abbreviated as "P(3HB)"), which is a homopolymer of 3-hydroxybutyric acid (hereinafter, abbreviated as "3HB"). P(3HB) is a thermoplastic polymer and it is biodegradable in nature. Thus, it has drawn attention as an environmentally friendly plastic material. Because of its high crystallinity, however, P(3HB) is hard and fragile. The range of practical applications thereof is accordingly limited. In order to expand the range of applications, it is necessary to impart P(3HB) with flexibility.

To this end, a PHA copolymer comprising 3HB and 3-hydroxyvaleric acid (hereinafter, abbreviated as "3HV") (hereinafter, such copolymer is abbreviated as "P(3HB-co-3HV)") and a method for producing the same have been developed (Patent Document 1 and Patent Document 2). Since P(3HB-co-3HV) had higher flexibility than P(3HB), it was considered that the range of applications of P(3HB-co-3HV) would be extensive. In practice, however, an increased 3HV molar fraction in P(3HB-co-3HV) does not lead to desirable physical changes. In particular, the flexibility of P(3HB-co-3HV) has not been sufficiently improved so as to be processed in the form of, for example, films, sheets, or soft-type packaging containers. Accordingly, the application of this material is limited to hard-type molded products, such as shampoo bottles or disposable razor handles.

Also, a PHA copolymer comprising 3HB and 3-hydroxyhexanoic acid (hereinafter, abbreviated as "3HH") (hereinafter, such copolymer is abbreviated as "P(3HB-co-3HH)") and a method for producing the same have been studied in order to further enhance PHA flexibility (Patent Document 3 and Patent Document 4). In related literature, P(3HB-co-3HH) was produced by fermentation using a wild-type strain of Aeromonas caviae isolated from soil and fatty acid, such as oleic acid or palmitic acid, as a carbon source, and the 3HH composition ratio of the resulting P(3HB-co-3HH) was 15 mol % when oleic acid was used as a carbon source and 5 mol % when palmitic acid was used as a carbon source.

Physical properties of P(3HB-co-3HH) have also been studied (Non-Patent Document 1). In this study, A. caviae is cultured using, as a single carbon source, a fatty acid containing 12 or more carbon atoms, and P(3HB-co-3HH) having a 3HH composition ratio of 11 mol % to 19 mol % is produced by fermentation. As the 3HH composition ratio is increased, the hard and fragile properties of P(3HB-co-3HH), as is the case with those of P(3HB), are gradually changed into flexible properties, and such flexible properties are superior to those of P(3HB-co-3HV). By changing the 3HH composition ratio, accordingly, an extensive range of physical properties that are applicable to polymers ranging from hard to soft polymers can be imparted to P(3HB-co-3HH). Thus, P(3HB-co-3HV) having a low 3HH composition ratio can be used for a product requiring rigidity, such as a television chassis, and P(3HB-co-3HV) having a high 3HH composition ratio can be used for a product requiring flexibility, such as a film. That is, an extensive range of applications can be expected.

Also, the PHA productivity of a transformant produced using, as a host, Cupriavidus necator (C. necator) and a PHA synthase expression plasmid, such as pJRDEE32 or pJRDEE32d13, into which pJRD215 (ATCC 37533) and a polyester synthase gene, the (R)-specific enoyl-CoA hydratase gene, or the like has been introduced has been investigated (Patent Document 5 and Non-Patent Document 2). While the amount of the cells was as low as 4 g/l after culture, it was found that polymer productivity would be improved via modification of cell culture conditions involving the use of plant oils and fats as carbon sources. For example, the amount of the cells would increase to 45 g/l, the polymer content would increase to 62.5%, and the 3HH composition ratio would increase to 8.1 mol %. Thus, attempts aimed at improvement of the 3HH composition ratio or polymer productivity of P(3HB-co-3HH) via culture techniques have been made (Patent Document 6). In general, however, plasmids would be deleted during the bacterial growth cycle as a result of introduction of a foreign gene using a plasmid. This destabilizes the introduced gene. Accordingly, such technique is not suitable for industrial production.

Meanwhile, it was reported that the 3HH composition ratio had improved via incorporation of the (R)-specific enoyl-CoA hydratase gene into the chromosome DNA of C. necator (Patent Document 7 and Non-Patent Document 3). According to this report, a plurality of (R)-specific enoyl-CoA hydratase genes may be inserted into a pha operon region comprising the pha synthase gene of C. necator, so as to increase the 3HH composition ratio to 10.5 mol %.

As described above, physical properties of P(3HB-co-3HH) vary in accordance with the 3HH composition ratio, and it can be thus used for an extensive range of applications. In order to attain desirable physical properties, however, it is necessary to precisely regulate the 3HH composition ratio. At the industrial level, in addition, it is preferable that a plurality of microorganism species be prepared for process simplification, so that a plurality of types of P(3HB-co-3HH) having different 3HH composition ratios can be produced under the same culture conditions. In the past, however, no improvement aimed at precise regulation of the 3HH composition ratio has been achieved in the breeding of microorganisms producing P(3HB-co-3HH).

PRIOR ART DOCUMENT

Patent Document

Patent Document 1: JP S57-150393 A (1982)
Patent Document 2: JP S59-220192 A (1984)
Patent Document 3: JP H5-93049 A (1993)
Patent Document 4: JP H7-265065A (1995)

Patent Document 5: JP H10-108682 A (1998)
Patent Document 6: JP 2001-340078 A
Patent Document 7: International Publication No. WO 2011/105379

Non-Patent Document

Non-Patent Document 1: Y. Doi, S. Kitamura, H. Abe, Macromolecules 28: 4822-4823, 1995
Non-Patent Document 2: T. Fukui, Y. Doi, J. Bacteriol., 179(15): 4821-4830, 1997
Non-Patent Document 3: Y. Kawashima et al., Appl. Environ. Microbiol., 78: 493-502, 2012

SUMMARY OF THE INVENTION

Problem to be Solved by the Invention

It is an object of the present invention to breed a microorganism that produces a polyhydroxyalkanoate (PHA) copolymer with a regulated monomer composition ratio, and it is another object to produce a polyhydroxyalkanoate (PHA) copolymer with regulated monomer composition ratio by fermentation using such microorganism.

Means for Solving the Problem

The present inventors have conducted concentrated studies in order to attain the above objects. As a result, they discovered that the monomer composition ratio of a PHA copolymer accumulated in a microorganism could be efficiently regulated by the controlled 3HH monomer synthetic pathway achieved by adjusting the expression of the (R)-specific enoyl-CoA hydratase gene inherent in the microorganism. This has led to the completion of the present invention.

Specifically, the present invention includes the following features.

(1) A microorganism comprising a (R)-specific enoyl-CoA hydratase gene in the genome DNA, characterized in that a nucleotide sequence upstream of the (R)-specific enoyl-CoA hydratase gene comprises a modification consisting of a substitution(s), a deletion(s), an insertion(s), and/or an addition(s) of one or a plurality of nucleotides so that the expression of the (R)-specific enoyl-CoA hydratase gene is regulated.

(2) The microorganism of (1), wherein the modification comprises a substitution(s) or an insertion(s) of one or a plurality of nucleotides in the nucleotide sequence of a promoter sequence, a Shine-Dalgarno (SD) sequence, or both thereof that enables regulation of the expression level of the (R)-specific enoyl-CoA hydratase gene.

(3) The microorganism of (1) or (2), wherein the nucleotide sequence upstream of the (R)-specific enoyl-CoA hydratase gene comprises a foreign promoter sequence introduced via substitution or insertion.

(4) The microorganism of any of (1) to (3), wherein the position of the substitution or insertion is within 10,000 nucleotides upstream of the (R)-specific enoyl-CoA hydratase gene.

(5) The microorganism of any of (1) to (4), which further comprises a polyhydroxyalkanoate synthase gene.

(6) The microorganism of (5), wherein the polyhydroxyalkanoate synthase gene is derived from *Aeromonas caviae*.

(7) The microorganism of any of (1) to (6), which belongs to the genus *Cupriavidus*.

(8) The microorganism of (7), which is *Cupriavidus* necator.

(9) The microorganism of any of (1) to (6), which belongs to the genus *Aeromonas*.

(10) The microorganism of (9), which is *Aeromonas hydrophila*.

(11) The microorganism of any of (1) to (10), wherein the nucleotide sequence upstream of the (R)-specific enoyl-CoA hydratase gene comprises one or more promoters selected from the group consisting of *E. coli*-derived promoters, phaC1 gene promoters, and modified phaC1 gene promoters, which have been introduced into the nucleotide sequence by substitution or insertion.

(12) The microorganism of any of (2) to (11), which further comprises an SD sequence downstream of the promoter sequence.

(13) The microorganism of (12), wherein the SD sequence is the sequence as shown by SEQ ID NO: 51 or 52.

(14) The microorganism of any of (1) to (13), wherein the (R)-specific enoyl-CoA hydratase gene forms an operon with another gene.

(15) The microorganism of any of (5) to (14), which is capable of producing a polyhydroxyalkanoate copolymer with a regulated monomer composition ratio.

(16) An expression regulatory DNA, which has a size of 30 bp to 900 bp and comprises a modified *Cupriavidus* necator phaC1 gene promoter, wherein the modified promoter comprises a nucleotide sequence selected from the group consisting of the nucleotide sequences as shown by SEQ ID NOs: 55 to 59.

(17) The expression regulatory DNA of (16), which further comprises a Shine-Dalgarno (SD) sequence of the phaC1 gene or a modified SD sequence thereof, provided that the SD sequence or modified SD sequence comprises any of the nucleotide sequences as shown by SEQ ID NOs: 51, 52, and 60 to 66.

(18) An expression regulatory DNA comprising a promoter consisting of the nucleotide sequence as shown by any of SEQ ID NOs: 47 to 50 and a nucleotide sequence as shown by any of SEQ ID NOs: 51, 52, and 60 to 66.

(19) The microorganism of any of (1) to (15), comprising the expression regulatory DNA of any of (16) to (18).

(20) A method for producing a polyhydroxyalkanoate copolymer, characterized in that the method comprises: culturing the microorganism of any of (5) to (15) and (19); and recovering a polyhydroxyalkanoate copolymer from the microorganism.

(21) The method of (20), wherein the polyhydroxyalkanoate copolymer comprises, as a constitutive unit, a 3-hydroxyhexanoic acid (3HH) monomer.

(22) The method of (21), wherein the polyhydroxyalkanoate copolymer is P(3HB-co-3HH).

Effect of the Invention

According to the present invention, a PHA copolymer having a desirable monomer composition ratio that is industrially useful can be produced by fermentation.

This description includes all or part of the contents disclosed in the description and/or drawings of Japanese Patent Application No. 2014-17873 and No. 2014-17879 that the present application claims priorities from.

MODES FOR CARRYING OUT THE INVENTION

Hereafter, the present invention is described in greater detail.

1. Microorganism Comprising (R)-Specific Enoyl-CoA Hydratase Gene in the Genome DNA, the Expression of which is Regulated The present invention provides a microorganism comprising a (R)-specific enoyl-CoA hydratase gene in the genome DNA, characterized in that a nucleotide sequence upstream of the (R)-specific enoyl-CoA hydratase gene comprises a modification consisting of a substitution(s), a deletion(s), an insertion(s), and/or an addition(s) of one or a plurality of nucleotides so that the expression of the (R)-specific enoyl-CoA hydratase gene is regulated.

The term "genome DNA" used herein refers to, for example, megaplasmid DNA (which may be simply referred to as "megaplasmid"), as well as chromosome DNA (which may be simply referred to as "chromosome"). Genome DNA is preferably a chromosome. Also, the "(R)-specific enoyl-CoA hydratase gene" used herein is a gene encoding the (R)-specific enoyl-CoA hydratase (PhaJ), which is an enzyme converting enoyl-CoA (i.e., an intermediate in fatty acid β oxidation) into (R)-3-hydroxyacyl CoA (i.e., a PHA monomer source).

A microorganism used in the present invention is not particularly limited, provided that such microorganism comprises the (R)-specific enoyl-CoA hydratase gene in genome DNA. It may be a wild-type microorganism that inherently comprises the (R)-specific enoyl-CoA hydratase gene, a mutant of such wild-type microorganism resulting from artificial mutagenesis, or a recombinant microorganism into which a foreign (R)-specific enoyl-CoA hydratase gene has been introduced in genome DNA via insertion or substitution in accordance with genetic engineering techniques. Specific examples of microorganisms include bacteria, yeasts, and filamentous fungi, preferably bacteria. Examples of preferable bacteria include those belonging to the genera *Ralstonia, Cupriavidus, Wautersia, Aeromonas, Escherichia, Alcaligenes*, and *Pseudomonas*. From the viewpoint of safety and productivity, bacteria belonging to the genera *Ralstonia, Cupriavidus, Aeromonas*, and Wautersia are more preferable; those belonging to the genera *Ralstonia* or *Aeromonas* are further preferable, and *Cupriavidus* necator or *Aeromonas hydrophila* are particularly preferable.

Examples of known (R)-specific enoyl-CoA hydratases derived from bacteria include those registered in the GenBank database open to the public at NCBI (U.S.A.), such as the (R)-specific enoyl-CoA hydratase derived from *A. caviae* (BAA21816) and the (R)-specific enoyl-CoA hydratases derived from *C. necator* (YP_725579.1, YP_728561.1, and YP_728829.1).

According to the present invention, a modification consisting of a substitution(s), a deletion(s), an insertion(s), and/or an addition(s) of one or a plurality of nucleotides is introduced at a site upstream of the (R)-specific enoyl-CoA hydratase gene in genome DNA of the microorganism, and the expression of the (R)-specific enoyl-CoA hydratase gene is regulated thereby. As long as the expression intensity of the (R)-specific enoyl-CoA hydratase gene can be changed (positively (+) or negatively (−), and preferably positively (±)) relative to the wild-type microorganism, such substitution, deletion, insertion, and/or addition are not particularly limited.

In an upstream region of the (R)-specific enoyl-CoA hydratase gene; a promoter sequence, an SD sequence, or both thereof that regulate the expression of the gene may comprise a mutation or mutations in one or a plurality of nucleotides. Alternatively, a nucleotide sequence other than the promoter sequence and the SD sequence may comprise a mutation or mutations in one or a plurality of nucleotides. Specifically, a modification (i.e., a substitution(s), a deletion(s), an insertion(s), and/or an addition(s) of one or a plurality of nucleotides, preferably a substitution(s) or an insertion(s)) may be introduced into a promoter sequence, an SD sequence, or another nucleotide sequence located within 10,000 nucleotides upstream of the gene (preferably a promoter sequence, an SD sequence, or both thereof) that is inherently present in an upstream region of the (R)-specific enoyl-CoA hydratase gene in genome DNA of the microorganism (that is, a wild-type), so as to change the expression intensity of the (R)-specific enoyl-CoA hydratase gene. Alternatively, DNA that enables regulation of the (R)-specific enoyl-CoA hydratase gene expression may be inserted into the nucleotide sequence located upstream of the (R)-specific enoyl-CoA hydratase gene in the genome DNA or such DNA may be introduced via substitution with any upstream nucleotide sequence, so as to regulate the expression intensity of the (R)-specific enoyl-CoA hydratase gene.

Preferable alternative techniques for efficiently regulating the expression intensity are, for example, substitution of a part of the nucleotide sequence at a site capable of regulating expression located in the vicinity of the translation initiation site upstream of the (R)-specific enoyl-CoA hydratase gene in genome DNA with an expression regulatory DNA comprising promoter sequence and/or SD sequence, or insertion of the expression regulatory DNA into such site.

For example, DNA comprising a promoter sequence, an SD sequence, or a modified sequence of such promoter sequence or SD sequence of the (R)-specific enoyl-CoA hydratase gene derived from the same or different microorganism species, or DNA comprising a promoter sequence, an SD sequence, or a modified sequence of such promoter sequence or SD sequence of a gene other than the (R)-specific enoyl-CoA hydratase gene derived from the same or different microorganism species, are within the scope of the expression regulatory DNA to be introduced (foreign expression regulatory DNA, in other words). As a promoter for the (R)-specific enoyl-CoA hydratase gene derived from the same microorganism species, a promoter sequence for a different (R)-specific enoyl-CoA hydratase gene of the same microorganism species may be used. Alternatively, a promoter sequence for the same (R)-specific enoyl-CoA hydratase gene of the same microorganism species may be introduced at a site different from the native position of the promoter. The same applies to the SD sequence of the same microorganism species.

The term "one or a plurality of nucleotides" used herein refers to one or a plurality of nucleotides in a nucleotide sequence located within 10,000 nucleotides upstream of the translation initiation site of the (R)-specific enoyl-CoA hydratase gene, comprising an expression regulatory region (which may comprise a promoter region and/or an SD sequence region, wherein the promoter region may comprise an operator sequence). For example, the term refers to one or several nucleotides, at least 20 to 50 nucleotides, at least 50 to 100 nucleotides, or at least 100 to 200 nucleotides. As used herein, the substitution(s), deletion(s), insertion(s), and/or addition(s) are introduction of a mutation or mutations of one or a plurality of nucleotides that enable the regulation of expression of the gene. The term "several" used herein refers to an integer from 2 to 10, preferably an integer from 2 to 7.

The term "enables the regulation of expression" or "capable of regulating expression" as used herein refers to regulating mRNA synthesis via transcription of the (R)-specific enoyl-CoA hydratase gene and subsequent protein synthesis, so as to become a degree that is substantially the same or greater or lesser than the degree of synthesis before modification. Such degree of synthesis is preferably potentiated.

Regarding the modification of an upstream region of the (R)-specific enoyl-CoA hydratase gene in genome DNA, methods of site-directed substitution or insertion of an arbitrary DNA in genome DNA are well known to a person skilled in the art. Representative examples of the methods include, but are not particularly limited to, the following methods: a method that utilizes mechanisms of transposon and homologous recombination (Ohman et al., J. Bacteriol., vol. 162: p. 1068, 1985); a method based on principles of site-directed integration caused by the mechanism of homologous recombination and elimination caused by the second homologous recombination (Nod et al., Methods Enzymol., vol. 154, p. 197, 1987); and, as an available example, a method in which, in the co-existence of the sacB gene derived from Bacillus subtilis, a microorganism strain from which a gene of interest has been eliminated by the second homologous recombination is easily isolated as a strain resistant to a sucrose-supplemented medium (Schweizer, Mol. Microbiol., vol. 6, p. 1195, 1992; Lenz et al., J. Bacteriol., vol. 176, p. 4385, 1994). As long as an arbitrary DNA can be inserted/substituted in the genome DNA, the methods are not particularly limited.

The terms "promoter" and "SD sequence" are generally defined as follows.

A "promoter" is a regulatory sequence that is associated with the efficiency of gene transcription initiation. In a broad sense, a promoter is a regulatory sequence that exists and functions at a site relatively close to a transcription initiation site, or it is a regulatory sequence that exists and functions at a site located at a distance from a transcription initiation site. In the case of procaryotes such as bacteria, for example, a promoter sequence generally comprises a region from the −35 region to the −10 region upstream of the gene transcription initiation site (+1), and the sequences of such regions often vary depending on prokaryote species. For example, the consensus sequences of the promoter in E. coli are known to be TTGACA (SEQ ID NO: 53) and TATAAT (SEQ ID NO: 54).

In general, an SD sequence is a region located several to a dozen nucleotides upstream of the gene translation site (+1), which is complementary or partially complementary to the 3° terminal region of 16S rRNA, a ribosome binds to mRNA at a part of the SD sequence, and translation starts from the translation initiation codon located immediately downstream thereof. That is, an SD sequence is located between the transcription initiation site and the translation initiation codon. In addition, an untranslated region upstream of the initiation codon in an mRNA comprising the SD sequence is generally referred to as 5' UTR, and it may occasionally affect mRNA stability. In the present invention, the term "SD sequence" refers to a ribosome binding sequence in mRNA located between the transcription initiation site and the translation initiation site of a structural gene and associated with translation of the structural gene (i.e., protein synthesis), and the term also refers to a DNA sequence encoding the ribosome binding sequence.

In the present invention, a site at which the expression regulatory region is to be modified (e.g., substituted or inserted) is not particularly limited, as long as the expression is regulated upstream of the genomic DNA region in which a (R)-specific enoyl-CoA hydratase gene of interest is present. It is preferable that substitution or insertion be performed at a site as close as possible to the (R)-specific enoyl-CoA hydratase gene. Alternatively, substitution or insertion may be performed at a site within 10,000 nucleotides upstream of the (R)-specific enoyl-CoA hydratase gene, preferably within 1,000 nucleotides upstream of the gene, more preferably within 500 nucleotides upstream of the gene, and particularly preferably within 50 nucleotides upstream of the gene.

Depending on the microorganism species, such as C. necator, the (R)-specific enoyl-CoA hydratase gene may occasionally form an operon with another metabolism-related gene or another gene of, for example, an enzyme associated with PHA synthesis. In such a case, it is most preferable that an expression regulatory sequence comprising a promoter and an SD sequence is externally introduced at a site between a structural gene present upstream of the (R)-specific enoyl-CoA hydratase gene and the (R)-specific enoyl-CoA hydratase gene by means of substitution or insertion, in order to efficiently and selectively regulate the expression of the (R)-specific enoyl-CoA hydratase gene without affecting the expression of another structural gene.

Some microorganisms, such as C. necator, occasionally comprise a plurality of (R)-specific enoyl-CoA hydratase genes. In such a case, target (R)-specific enoyl-CoA hydratase genes subjected to expression regulation are not particularly limited, and one or more of the plurality of (R)-specific enoyl-CoA hydratase genes may be subjected to expression regulation. In addition, C. necator originally comprises a chromosome and a megaplasmid as genome DNAs, a target (R)-specific enoyl-CoA hydratase gene subjected to expression regulation in the present invention may be present in either chromosome or megaplasmid, preferably in chromosome.

In the present invention, a promoter sequence and an SD sequence to be comprised in an expression regulatory sequence subjected to modification (or mutation), such as substitution or insertion, in an upstream region of the (R)-specific enoyl-CoA hydratase gene are not particularly limited, and any sequence can be used, as long as it can regulate the expression of the (R)-specific enoyl-CoA hydratase gene. The aforementioned promoter sequence and SD sequence may be the same or different from those inherent in a microorganism of interest, or such promoter sequence and SD sequence may be derived from a microorganism species (e.g., a different genus, species, or strain) that is different from a microorganism species of interest, or alternatively a promoter sequence and an SD sequence modified therefrom may be used. In the present invention, a promoter to be comprised in expression regulatory DNA is not particularly limited. Examples of the promoter include a phaC1 promoter (REP) for the PHA synthase gene of C. necator (i.e., the phaC1 gene), a modified phaC1 promoter (modified REP) obtained by altering a sequence (or sequences) of the −35 region and/or the −10 region of the phaC1 promoter (REP) or a sequence of a region therebetween via substitution, deletion, insertion, and/or addition of at least one nucleotide, and known E. coli-derived promoters, such as a trc promoter as shown by SEQ ID NO: 47, an lac promoter as shown by SEQ ID NO: 49, an lacUV5 promoter as shown by SEQ ID NO: 50, and a trp promoter as shown by SEQ ID NO: 48. E. coli-derived promoters, such as a ire promoter, an lacUV5 promoter, and a trp promoter, are particularly preferable since these promoters have high potential to enhance the expression of the (R)- specific enoyl-CoA hydratase gene. An example of modified REP is a promoter comprising the nucleotide sequence as shown by any of SEQ ID NOs: 55 to 59, and a promoter comprising the nucleotide sequence as shown by SEQ ID NO: 59 is preferable.

Modified REP is described in greater detail.

Modified REP can be obtained by modifying a sequence of the phaC1 promoter (REP), which is a promoter for the phaC1 gene that is the PHA synthase gene of *C. necator*. The phaC1 gene forms operons with the phaA gene and the phaB1 gene and is present in the genome DNA. Thus, the phaC1 promoter (REP) is also referred to as the "pha operon promoter."

In the present invention, the phaC1 promoter (REP) subjected to modification preferably comprises a nucleotide sequence as shown by SEQ ID NO: 67 derived from the *C. necator* H16 strain (TTGACAGCGCGTGCGTTG-CAAGGCAACAAT). In the phaC1 promoter (REP), the −35 region and the −10 region comprise 6 nucleotides from nucleotide 1 (e.g., TTGACA, which is the same sequence as SEQ ID NO: 53) and 6 nucleotides from nucleotide 25 (e.g., AACAAT, SEQ ID NO: 68), respectively.

Modified REP can be obtained via substitution, addition, insertion, and/or deletion (preferably, substitution) of one or several and preferably 1 to 4 nucleotides in the −35 region and the −10 region of the phaC1 promoter derived from *C. necator*. Alternatively, modified REP can be obtained by altering the distance between the −35 region and the −10 region via deletion or addition of one or several and preferably 1 or 2 nucleotides. Modified REP has promoter activity.

The term "several" used herein refers to an integer from 2 to 10, such as an integer from 2 to 7, an integer from 2 to 5, an integer from 2 to 4, or an integer from 2 or 3.

The term "having promoter activity" used herein refers to an ability that an RNA polymerase binds to a promoter and is capable of initiating transcription (mRNA synthesis).

Modified REP is, for example, a promoter comprising a nucleotide sequence as shown by any of SEQ ID NOs: 55 to 59. The nucleotide sequences as shown by SEQ ID NOs: 55 to 59 are modified phaC1 promoter sequences of the *C. necator* H16 strain. In the case of a different strain, accordingly, modified REP comprises a sequence derived from a wild-type promoter sequence of the strain by substitution, addition, insertion, and/or deletion of one or several and preferably 1 to 4 nucleotides, which may be different from the nucleotide sequences as shown by SEQ ID NOs: 55 to 59.

Modified REP has an altered promoter activity or transcription efficiency in comparison with the wild-type phaC1 promoter (REP) as a result of substitution, addition, insertion, and/or deletion of the nucleotides described above. Modified REP is accordingly useful for regulation of structural gene expression intensity. The term "altered promoter activity" used herein refers to any of the following: enhanced activity compared with the wild-type phaC1 promoter (REP); equivalent activity; activity lowered by at most 80%; or activity realizing a gene expression level enhanced, equivalent to, or lowered by at most 80% in comparison with the gene expression level attained when the wild-type phaC1 promoter is used. Accordingly, modified REP of interest can be adequately selected in accordance with the purpose of use.

The phaC1 promoter (REP) can be modified in accordance with, for example, the procedures described below.

A nucleic acid comprising a sequence derived from the phaC1 promoter (REP) sequence by substitution, addition, insertion, and/or deletion of one or several and preferably 1 to 4 nucleotides may be synthesized in accordance with known methods, such as mutagenesis via PCR, site-directed mutagenesis, or automated nucleic acid synthesis. Briefly, mutagenesis via PCR that is generally employed may be performed using mutagenesis primers. Such mutagenesis primers may be prepared by designing oligonucleotides capable of specifically amplifying a target nucleic acid and introducing a nucleotide mutation of interest (i.e., substitution, addition, insertion, and/or deletion) thereinto in accordance with conventional techniques. The conditions for amplification via PCR are not particularly limited, as long as a nucleic acid comprising a modified promoter can be amplified. Specifically, a plasmid, which has been inserted with double-stranded DNA of at least 30 bp to 900 bp (e.g., approximately 30 bp to 1,200 bp) comprising a promoter sequence derived from the wild-type phaC1 gene, is constructed, sense and antisense primers for mutagenesis are annealed to flank the target nucleotide sequences of the DNA to be amplified, and an amplification cycle is repeated 20 to 40 times.

While an SD sequence comprised in an expression regulatory sequence is not particularly limited in the present invention, for example, the SD sequence includes: an SD sequence of the phaC1 gene as shown by SEQ ID NO: 51 (i.e., the phaC1 SD sequence); and a modified phaC1 SD sequence resulting from substitution of at least one nucleotide in such phaC1 SD sequence. A modified phaC1 SD sequence is not particularly limited, and examples thereof include modified SD sequences as shown by SEQ ID NO: 52 (TCTCTCT), SEQ ID NO: 60 (TGTGAGA), SEQ ID NO: 61 (ATATAGA), SEQ ID NO: 62 (AGTGAGA), SEQ ID NO: 63 (TGTGTGA), SEQ ID NO: 64 (TGAGTGA), SEQ ID NO: 65 (AGAGATA), and SEQ ID NO: 66 (AGA-TAGA), preferably the modified SD sequence as shown by SEQ ID NO: 52.

The modified SD sequence is hereinafter described in greater detail.

A modified SD sequence may be obtained by modifying, for example, the phaC1 SD sequence, which was predicted by A. Steinbuchel et al. (J. Bacterial., 1991, 173 (1): 168). In such a case, the phaC1 SD sequence to be modified is located approximately 17-nucleotides upstream from the translation initiation site of the phaC1 gene in the genome DNA of *C. necator*. Specifically, such sequence is the nucleotide sequence "AGAGAGA" (SEQ ID NO: 69).

A modified SD sequence is a "modified phaC1 SD sequence" obtained by substitution of one or several and preferably 1 to 7 nucleotides in the SD sequence of the phaC1 gene described above. A specific example of the modified phaC1 SD sequence is DNA comprising the nucleotide sequence as shown by any of SEQ ID NOs: 52 and 60 to 66.

A modified phaC1 SD sequence has an altered translation activity and/or mRNA stability as a result of the nucleotide substitution, in comparison with those attained using the wild-type phaC1 SD sequence. Accordingly, such sequence is useful for regulation of structural gene expression intensity. The term "altered translation activity and/or mRNA stability" used herein refers to any of the following: enhanced activity and/or stability compared with the wild-type phaC1 SD sequence; equivalent activity and/or stability; activity and/or stability lowered by, for example, at most 60%, 40%, or 25%; or activity realizing a gene expression level (or a protein production level) enhanced, equivalent to, or lowered by at most 60%, 40%, or 25%, in comparison with those attained when the wild-type phaC1 SD sequence is used. A modified phaC1 SD sequence can be adequately selected according to need.

A modified phaC1 SD sequence; that is, a nucleic acid comprising a mutation such as nucleotide substitution introduced into the phaC1 SD sequence, can be synthesized in accordance with known methods, such as mutagenesis via PCR, site-directed mutagenesis, or automated nucleic acid synthesis, as described above. For example, PCR can be carried out using mutagenesis primers. Such mutagenesis primers may be prepared by designing oligonucleotides capable of specifically amplifying a target gene fragment and introducing a nucleotide mutation of interest (i.e., substitution, addition, insertion, and/or deletion) thereinto in accordance with known methods. The conditions for amplification via PCR are not particularly limited, provided that a target nucleic acid can be amplified.

An SD sequence is located between the transcription initiation site and the translation initiation site as an expression regulator, which is several to a dozen nucleotides upstream of the translation initiation site. An untranslated region upstream of the initiation codon comprising an SD sequence is generally referred to as "5' UTR," and it occasionally affects mRNA stability. Thus, a mutation may be introduced into the SD sequence or 5' UTR comprising the same, so that mRNA stability may be altered, and the gene expression intensity may be altered as a consequence. In the present invention, the term "SD sequence" refers to a ribosome binding sequence on mRNA located between the transcription initiation site and the translation initiation site of a structural gene and associated with translation of the structural gene (protein synthesis) and a DNA sequence encoding the ribosome binding sequence.

In the present invention, expression regulatory DNA preferably comprises a promoter and an SD sequence as exemplified above.

In such expression regulatory DNA, a promoter and an SD sequence are adequately positioned to exert promoter functions and ribosome binding functions. Thus, it can be used for gene expression. As described above, in addition, the promoter and the SD sequence regulate different steps of gene expression. Thus, expression regulatory DNA comprising the modified REP in combination with the known SD sequence or expression regulatory DNA comprising the modified SD sequence in combination with the known promoter can be prepared and used. The expression regulatory DNA of the present invention may comprise adequate DNA associated with expression regulation, in addition to the promoter and the SD sequence. For example, the expression regulatory DNA may comprise a nucleotide sequence of at most 900, 500, 300, or 200 nucleotides upstream of the phaC1 gene or a nucleotide sequence of at most 900, 500, 300, or 200 nucleotides upstream of a structural gene to be subjected to expression regulation. While such nucleotide sequence may comprise more than 900 nucleotides as long as it is associated with expression regulation, a nucleotide sequence comprising at most 900 nucleotides is more preferable.

In the expression regulatory DNA, positions at which the promoter and the SD sequence are to be inserted can be determined by known methods. For example, fragments comprising such sequences are amplified by PCR, the resulting amplified fragments are cleaved with adequate restriction enzymes, and the cleaved fragments are bound to adequate positions. An "adequate position" is not particularly limited, as long as the expression regulatory DNA can regulate the expression of a structural gene to be subjected to expression regulation in a region upstream of the structural gene. It is preferable that the expression regulatory DNA be bound to a position as close as possible to the structural gene of interest. When the structural gene is in genome DNA, for example, the expression regulatory DNA may be bound by substitution or insertion at a site within at most 10,000 nucleotides, preferably at most 1,000 nucleotides, more preferably at most 500 nucleotides, and particularly far preferably at most 50 nucleotides upstream of the genome DNA region.

When a structural gene of interest forms an operon together with another structural gene as in the case of the (R)-specific enoyl-CoA hydratase gene of for example, C. necator, it is preferable that the expression regulatory sequence be bound via substitution or insertion to a site between the structural gene and another structural gene present upstream of the structural gene, in order to efficiently and selectively regulate the expression of the structural gene without affecting the expression of other structural genes. When all structural genes constituting an operon are to be subjected to expression regulation, it is preferable that the expression regulatory sequence be bound to the operon via substitution or insertion at a promoter region inherent in the operon or a site in the vicinity thereof.

When a vector, such as a plasmid, phage, phagemid, or cosmid vector, is constructed using the expression regulatory sequence in combination with a structural gene of interest, the promoter in the expression regulatory sequence is not particularly limited, as long as it can regulate the expression of the structural gene at a site upstream of the structural gene. Such promoter is preferably bound at a position relatively close to the target structural gene. For example, the promoter may be bound via substitution or insertion at a site within at most 10,000 nucleotides, preferably at most 1,000 nucleotides, more preferably at most 500 nucleotides, and particularly far preferably at most 100 nucleotides upstream of the structural gene. In addition, the SD sequence is associated with activity of translation from mRNA into a protein. Accordingly, it is necessary that the SD sequence be located at a site between the transcription initiation site and the translation initiation site downstream of the promoter. For example, the SD sequence is preferably located several to a dozen nucleotides upstream of the translation initiation site of the gene.

It is preferable that the expression regulatory DNA comprises, for example, the SD sequence of the phaC1 gene as shown by SEQ ID NO: 51 or a modified SD sequence thereof comprising the nucleotide sequence as shown by any of SEQ ID NOs: 52 and 60 to 66 at an adequate site downstream of the promoter sequence as shown by any of SEQ ID NOs: 47 to 50. While the expression regulatory DNA may comprise any DNA sequence in addition to the promoter region and the SD region, such DNA sequence is not particularly limited. Examples of expression regulatory DNAs having a modification, such as a substitution or an insertion, or a mutation at a site upstream of the (R)-specific enoyl-CoA hydratase gene include, but are not limited to, those comprising the nucleotide sequences as shown by SEQ ID NOs: 37 to 45.

According to one embodiment of the present invention, the expression regulatory DNA comprises: a promoter consisting of the nucleotide sequence as shown by any of SEQ ID NOs: 47 to 50; or a modified REP comprising the nucleotide sequence as shown by any of SEQ ID NO: 55 to 59 and the phaC1 SD sequence as shown by SEQ ID NO: 51 or a modified phaC1 SD sequence as shown by any of SEQ ID NO 52 and 60 to 66. As described above, the SD sequence is located at an adequate site downstream of the promoter. DNAs like the promoter, the modified REP, the phaC1 SD sequence, the modified phaC1 SD sequence, and the expression regulatory DNA can be produced using, for example, an automated nucleic acid synthesizer or can be amplified by nucleic acid amplification techniques including PCR techniques.

When the microorganism in which the (R)-specific enoyl-CoA hydratase gene expression is regulated according to the present invention is used for the production of a PHA copolymer, it is necessary that such microorganism comprises the PHA synthase gene, in addition to the (R)-specific enoyl-CoA hydratase gene. In such a case, a microorganism that inherently has both the (R)-specific enoyl-CoA hydratase gene and the PHA synthase gene, or a microorganism into which either or both the (R)-specific enoyl-CoA hydratase gene and the PHA synthase gene has (or have) been introduced by genetic engineering techniques, may be used in the present invention. The PHA synthase gene may be present in the chromosome, plasmid, or megaplasmid inherent in the microorganism, or it may be present in a foreign vector, such as a plasmid, phage, or phagemid vector. The PHA synthase gene is preferably present in the chromosome, plasmid, or megaplasmid, and it is more preferably present in the chromosome. While the PHA synthase gene is not particularly limited, a gene encoding a PHA synthase capable of synthesizing a PHA copolymer having a monomer unit of 6 or more carbon atoms is preferable, and a gene encoding a PHA synthase capable of synthesizing a PHA copolymer comprising a 3HH monomer as a constitutive unit is more preferable. Such PHA synthase gene is preferably a PHA synthase gene derived from *A. caviae*, and it is more preferably, for example, a PHA synthase gene inherent in a wild-type *A. caviae* strain (i.e., phaC gene), a mutant enzyme gene thereof that encodes the amino acid sequence as shown by SEQ ID NO: 46, or a gene comprising an amino acid sequence having 85% or higher sequence identity with the amino acid sequence as shown by SEQ ID NO: 46 and encoding a PHA synthase capable of synthesizing a PHA copolymer that comprises a 3HH monomer. Sequence identity is more preferably 90% or higher, further preferably 95% or higher, and still further preferably 98% or higher.

Examples of PHA-producing microorganisms comprising the (R)-specific enoyl-CoA hydratase gene and capable of synthesizing a PHA copolymer that comprises a 3HH monomer are microorganisms preferably derived from *C. necator*, and more preferably derived from the *C. necator* H16 strain, via introduction of a PHA synthase gene comprising a nucleotide sequence encoding the amino acid sequence as shown by SEQ ID NO: 46 derived from *A. caviae*.

A method for producing a microorganism capable of producing a PHA copolymer comprising a 3HH monomer as a constitutive unit is not particularly limited, and an example of a method involving the use of *C. necator* as a host is described below. The PHA synthase gene derived from *A. caviae* is substituted with the PHA synthase gene of *C. necator* by homologous recombination or other means in the genome DNA of *C. necator*. The expression regulatory DNA comprising the promoter and the SD sequence is then inserted into the nucleotide sequence located upstream of the inherent (R)-specific enoyl-CoA hydratase gene in the genome DNA by homologous recombination or other means.

According to the homologous recombination, a vector comprising homologous nucleotide sequences upstream and/or downstream of the site of gene introduction at the locus in genome DNA in addition to the nucleic acid sequence selected from the gene to be introduced, the promoter, the SD sequence, and the expression regulatory sequence is used to transform the target microorganism by known methods, such as the calcium chloride method, electroporation, the polyethylene glycol method, or the spheroplast method, and the nucleic acid element of interest may be introduced into the target gene locus in genome DNA. Examples of vectors that can be used include plasmid, phage, and phagemid vectors. A vector may further comprise a marker gene used for selecting a microorganism of interest, such as tetracycline tolerant gene, ampicillin tolerant gene, or kanamycin tolerant gene, and terminator. Genetic cloning or genetic recombination techniques can be performed in accordance with the techniques described in, for example, Sambrook, J. et al., Molecular Cloning, A Laboratory Manual, Cold Spring Harbor Laboratory Press, 1989 or 2001.

In order to analyze an expression activity of a target gene in the genome DNA of a microorganism into which the modified promoter and/or the modified SD sequence have been introduced, the techniques as described below may be employed.

Gene expression activity of the modified phaC1 promoter (modified REP) and that of the modified phaC1 SD sequence may be evaluated by ligating reporter genes at sites downstream of the promoter and the SD sequence, respectively, and measuring the expression level of the reporter gene by known methods. A reporter gene may be used without particular limitation. Examples of reporter gene include genes enabling enzyme activity measurement, such as β galactosidase gene and acidic phosphatase gene, and proteins enabling relative and indirect measurement of gene expression levels, such as fluorescent proteins (e.g., GFP and EGFP) and luminescent proteins (e.g., luciferase). Alternatively, regarding the production of, for example, P(3HB-co-3HH) by a *C. necator* strain, the 3HH composition is increased in a recombinant in which the copy number of the (R)-specific enoyl-CoA hydratase genes (i.e., the phaJ genes) is increased. As such, a *C. necator* strain into which a plasmid vector comprising a sequence of a gene such as phaJ gene ligated downstream of the promoter and the SD sequence and have been introduced, may be used to produce P(3HB-co-3HH), followed by analyzing the 3HH composition of the product to presume a gene expression activity of the promoter and the SD sequence.

A polyhydroxyalkanoate (PHA) copolymer with regulated monomer composition ratio can be produced using the microorganism according to the present invention. In the past, no techniques for fermentation of microorganisms in which the monomer composition ratio of the PHA copolymer could be freely regulated were known. The microorganisms according to the present invention, however, can be made to have various monomer composition ratios through the modification of expression regulatory sequences. Examples of PHA copolymers include, but are not limited to, a copolymer of 3-hydroxybutyric acid (3HB) and 3-hydroxyhexanoic acid (3HH), and a copolymer of 3-hydroxybutyric acid (3HB) and 3-hydroxyoctanoic acid (3HO), and the carbon number of such monomer is unlimitedly, for example, at least 4 to 8 carbon atoms. When a PHA copolymer is, for example, P(3HB-co-3HH), the 3HH monomer composition ratio (mol %) in the copolymer can be regulated to between about 5 and about 15. According to the present invention, the 3HH monomer composition ratio (mol %) of P(3HB-co-3HH) may be adjusted, preferably to about 6 to about 15, more preferably to about 8 to about 13, and further preferably to about 9 to about 12. Thus, a biodegradable polymer having high versatility and flexibility can be produced. In the present invention, a PHA copolymer comprising the 3-hydroxyhexanoic acid (3HH) monomer as a constitutive unit is preferable, and P(3HB-co-3HH) having the monomer composition ratio as described above is particularly preferable.

2. Method for Producing Polyhydroxyalkanoate Copolymer

The present invention also provides a method for producing a polyhydroxyalkanoate copolymer, characterized in that the method comprises: culturing the microorganism; and recovering a polyhydroxyalkanoate (PHA) copolymer from the microorganism.

In the present invention, the PHA copolymer is produced by culturing the microorganism with regulated (R)-specific enoyl-CoA hydratase gene expression, which comprises the PHA synthase gene, and allowing the PHA copolymer to accumulate in the microorganism.

At the time of culture, any carbon sources may be used, as long as the PHA-producing microorganisms according to the present invention are assimilable. Preferable examples include: saccharides, such as glucose, fructose, and sucrose; oil and fats, such as palm oil, palm kernel oil, corn oil, coconut oil, olive oil, soybean oil, rapeseed oil, Jatropha oil, fractionated products of any oils and fats, and refined by-products of any oils and fats; fatty acids, such as lauric acid, oleic acid, stearic acid, palmitic acid, and myristic acid, and derivatives of the fatty acids. More preferably, in addition to plant-derived oil and fats, such as palm oil and palm kernel oil, palm kernel olein, which is a low-temperature-melting fraction separated from palm kernel oil, may be used. Furthermore, from the viewpoint of avoiding the conflict with the food use, refined byproducts of oil and fats, such as palm fatty acid distillate (PFAD palm kernel fatty acid distillate (PKFAD), and rapeseed oil fatty acid distillate, may also be used. When producing PHA according to the present invention, the microorganisms are preferably cultured using a medium containing the carbon sources, the nitrogen sources which are nutrients other than the carbon sources, inorganic salts, and other organic nutrients. Examples of nitrogen sources include ammonium salts, such as ammonia, ammonium chloride, ammonium sulfate, and ammonium phosphate, peptone, meat extract, and yeast extract. Examples of inorganic salts include potassium dihydrogenphosphate, disodium hydrogen-phosphate, magnesium phosphate, magnesium sulfate, and sodium chloride. Examples of other organic nutrients include amino acids, such as glycine, alanine, serine, threonine, and proline, and vitamins, such as vitamin B1, vitamin B12, and vitamin C.

Conditions for culturing the microorganisms, such as culture temperature, culture time, pH during culture, and medium, may be the same as those generally used for culturing bacteria belonging to, for example, the genera *Ralstonia, Cupriavidus, Wautersia, Aeromonas, Escherichia, Alcaligenes,* or *Pseudomonas.*

In the present invention, PHA copolymers may be recovered from microorganisms without particular limitation. For example, PHA copolymers may be recovered in the manner described below. After the completion of culture, microorganisms are separated from the culture fluid using a centrifuge or the like, and the microorganisms are washed with distilled water and methanol, or the like, followed by drying them. PHA copolymers are extracted from the dried microorganisms using an organic solvent such as chloroform. Microbial components are removed from the organic solvent containing PHA copolymers by filtration or other means, and a poor solvent, such as methanol or hexane, is added to the filtrate, so as to allow the PHA copolymers to precipitate. Subsequently, the supernatant is removed by filtration or centrifugation, the remnant is dried, and PHA copolymers are then recovered.

The weight average molecular weight (Mw) of the obtained PHA copolymers and the composition of a monomer such as 3HH (mol %) can be analyzed by, for example, gas chromatography or nuclear magnetic resonance measurement.

A PHA copolymer produced in the present invention is preferably a PHA copolymer comprising 3HH monomer as a constitutive unit, more preferably P(3HB-co-3HH) comprising 3HB monomer and 3HH monomer as constitutive units, further preferably P(3HB-co-3HH) having a 3HH composition ratio of from 5 mol % to 15 mol %. In the PHA copolymer obtained in the present invention, the monomer ratio, such as 3HH composition ratio, is regulated. Thus, an extensive range of physical properties that are applicable to polymers ranging from hard polymers to soft polymers can be imparted to the above-mentioned copolymers.

EXAMPLES

Hereafter, the present invention is described in detail with reference to the examples; however, the technical scope of the present invention is not limited to these examples. In general, genetic engineering can be performed in the manner as described in Molecular Cloning (Cold Spring Harbor Laboratory Press, 1989). Enzymes, cloning hosts, and other materials used for genetic engineering can be purchased from commercial suppliers and used in accordance with manufacturer's instructions. Any enzymes can be used without particular limitation, as long as such enzymes can be used for genetic engineering.

[Production Example 1] Preparation of KNK005Δpha Z1,2,6 Strain

At the outset, plasmids for gene disruption were prepared in the manner described below.

PCR was carried out using chromosome DNA of the *C. necator* H16 strain as a template and the primers as shown by SEQ ID NO: 1 and SEQ ID NO: 2. A PCR cycle of (1) 98° C. for 2 minutes and (2) 98° C. for 15 seconds, 60° C. for 30 seconds, and 68° C. for 2 minutes was repeated 25 times, and KOD-plus-polymerase (manufactured by Toyobo Co., Ltd.) was used. Also, PCR was carried out using the primers as shown by SEQ ID NO: 3 and SEQ ID NO: 4. In addition, PCR was carried out using the two types of DNA fragments obtained as a result of the PCR procedures described above as templates and the primers as shown by SEQ ID NO: 1 and SEQ ID NO: 4 under the same conditions, and the resulting DNA fragments were digested with the restriction enzyme SwaI. The DNA fragment was ligated to the pNS2X-sacB vector (described in JP 2007-259708 A) digested with SwaI with the aid of a DNA ligase (Ligation High; manufactured by Toyobo Co., Ltd.). Thus, the plasmid vector for gene disruption (pNS2X-pha Z6(−+)) comprising the nucleotide sequences located upstream and downstream of the pha Z6 structural gene was prepared.

In addition, PCR was carried out under the same conditions using chromosome DNA of the *C. necator* H16 strain as a template and the primers as shown by SEQ ID NO: 5 and SEQ ID NO: 6. Also, PCR was carried out under the same conditions using the primers as shown by SEQ ID NO: 7 and SEQ ID NO: 8. Further, PCR was carried out under the same conditions using the two types of DNA fragments obtained as a result of the PCR procedures described above as templates and the primers as shown by SEQ ID NO: 5 and 8. The resulting DNA fragment was digested with the restriction enzyme SwaI. The DNA fragment was ligated to the pNS2X-sacB vector (described in JP 2007-259708 A) digested with SwaI with the aid of a DNA ligase (Ligation High; manufactured by Toyobo Co., Ltd.). Thus, the plasmid vector for gene disruption (pNS2X-pha Z1(−+)) comprising the DNA sequences located upstream and downstream of the pha Z1 structural gene was prepared.

Further, PCR was carried out under the same conditions using chromosome DNA of the *C. necator* H16 strain as a template and the primers as shown by SEQ ID NO: 9 and SEQ ID NO: 10. Also, PCR was carried out under the same conditions using the primers as shown by SEQ ID NO: 11 and SEQ ID NO: 12. In addition, PCR was carried out under the same conditions using the two types of DNA fragments obtained as a result of the PCR, procedures described above as templates and the primers as shown by SEQ ID NO: 9 and 12. The resulting DNA fragment was digested with the restriction enzyme SwaI. The DNA fragment was ligated to the pNS2X-sacB vector (described in JP 2007-259708 A) digested with SwaI with the aid of a DNA ligase (Ligation High; manufactured by Toyobo Co., Ltd.). Thus, the plasmid vector for gene disruption (pNS2X-pha Z2(−+)) comprising the DNA sequences located upstream and downstream of the pha Z2 structural gene was prepared.

Subsequently, gene-disrupted strains were prepared.

The *E. coli* S17-1 strain (ATCC47055) was transformed with the plasmid vector for gene disruption (pNS2X-pha Z6(−+)), and the transformed strain was subjected to mixed culture with the KNK005 strain (see U.S. Pat. No. 7,384,766) in a nutrient agar medium (manufactured by Difco) to perform conjugal transfer. The KNK005 strain is a *C. necator* H16 strain into which a gene encoding a PHA synthase comprising the amino acid sequence as shown by SEQ ID NO: 46 in the sequence listing has been introduced.

The culture was seeded on the Simmons' agar medium containing 250 mg/l kanamycin (2 g/l sodium citrate, 5 WI sodium chloride, 0.2 g/l magnesium sulfate.7H$_2$O, 1 g/l ammonium dihydrogenphosphate, 1 g/l dipotassium hydrogenphosphate, 15 g/l agar, pH 6.8), the strains grown on the agar medium were selected, and the strains comprising the plasmid integrated into the chromosome of the KNK005 strain were obtained. These strains were cultured in the nutrient broth medium (manufactured by Difco) over two generations, the cultured strains were diluted and applied to a 15% sucrose-containing nutrient agar medium, and the grown strains were obtained as strains from which the plasmid had been removed. PCR based analysis was further conducted, so as to isolate a strain lacking a region from the initiation codon to the termination codon of the pha Z6 gene on the chromosome. This gene-disrupted strain was designated as the KNK005Δpha Z6 strain. The obtained KNK005Δpha Z6 strain lacks a region from the initiation codon to the termination codon of the pha Z6 gene on the chromosome of the *C. necator* H16 strain, and this strain comprises a gene encoding a PHA synthase comprising the amino acid sequence as shown by SEQ ID NO: 46 in the sequence listing introduced into the chromosome.

In the same manner as described above, the chromosome gene-disrupted strain (the KNK005Δpha Z2,6 strain) lacking a region from the initiation codon to the termination codon of the pha Z6 gene and a region from codon 16 to the termination codon of the pha Z2 gene from the chromosome was prepared from the KNK005Δpha Z6 strain as a parent strain using pNS2X-pha Z2(−±). Further, the gene-disrupted strain (the KNK005Δpha Z1,2,6 strain) lacking a region from the initiation codon to the termination codon of the pha Z6 gene, a region from the initiation codon to the termination codon of the pha Z1 gene, and a region from codon 16 to the termination codon of the pha Z2 gene from the chromosome was prepared from the KNK005Δpha Z2,6 strain as a parent strain in the same manner as described above using pNS2X-pha Z1(−+). The resulting KNK005Δpha Z1,2,6 strain lacks a region from the initiation codon to the termination codon of the pha Z6 gene, a region from the initiation codon to the termination codon of the pha Z1 gene, and a region from codon 16 to the termination codon of the pha Z2 gene from the chromosome of the *C. necator* 6 strain. The KNK005Δpha Z1,2,6 strain also comprises a gene encoding a PHA synthase comprising the amino acid sequence as shown by SEQ ID NO: 46 in the sequence listing introduced into the chromosome.

[Production Example 2] Preparation of KNK005 trc-phaJ4b/Δpha Z1,2,6 Strain

At the outset; a plasmid used for insertion of promoter and SD sequence was prepared in the manner described below.

PCR was carried out under the same conditions as with Production Example 1 using chromosome DNA of the *C. necator* H16 strain as a template and the primers as shown by SEQ ID NO: 13 and SEQ ID NO: 14. Also, PCR was carried out under the same conditions using the primers as shown by SEQ ID NO: 15 and SEQ ID NO: 16. Further, PCR was carried out under the same conditions using the pKK388-1 plasmid (manufactured by Clontech Laboratories, Inc.) as a template and the primers as shown by SEQ ID NO: 17 and SEQ ID NO: 18. In addition, PCR was carried out under the same conditions using the three types of DNA fragments obtained as a result of the PCR procedures described above as templates and the primers as shown by SEQ ID NO: 13 and SEQ ID NO: 16. The resulting DNA fragment was digested with the restriction enzyme SwaI. The DNA fragment was ligated to the pNS2X-sacB vector (described in JP 2007-259708 A) digested with SwaI with the aid of a DNA ligase (Ligation High; manufactured by Toyobo Co. Ltd.). Thus, a plasmid vector for DNA insertion comprising the nucleotide sequence upstream of the phaJ4b structural gene, the trc promoter, the phaC1 SD sequence, and the phaJ4b structural gene sequence was prepared (i.e., pNS2X-sacB+phaJ4bU-trc-phaJ4b).

Subsequently, a strain used for insertion of promoter and SD sequence was prepared.

The *E. coli* S17-1 strain (ATCC47055) was transformed with the plasmid vector for promoter and SD sequence insertion (pNS2X-sacB+phaJ4bU-trc-phaJ4b), and the transformed strain was subjected to mixed culture with the KNK005Δpha Z1,2,6 strain prepared in Production Example 1 in a nutrient agar medium (manufactured by Difco) to perform conjugal transfer. The culture was seeded on the Simmons' agar medium containing 250 mg/l kanamycin (2 g/l sodium citrate, 5 g/l sodium chloride, 0.2 g/l magnesium sulfate.7H$_2$O, 1 g/l ammonium dihydrogenphosphate, 1 g/l dipotassium hydrogenphosphate, 15 g/l agar, pH 6.8), the strains grown on the agar medium were selected, and the strains comprising the plasmid incorporated into the chromosome of the KNK005Δpha Z1,2,6 strain were obtained. These strains were cultured in the nutrient broth medium (manufactured by Difco) over two generations, the cultured strains were diluted and applied to a 15% sucrose-containing nutrient agar medium, and the grown strains were obtained as strains from which the plasmid had been removed. PCR based analysis was further conducted, so as to isolate a strain comprising a DNA fragment comprising the trc promoter and the phaC1 SD sequence as shown by SEQ ID NO: 38 inserted into a site upstream of the phaJ4b structural gene on the chromosome. This strain used for insertion of promoter and SD sequence was designated as the KNK005 trc-phaJ4b/Δpha Z1,2,6 strain.

[Production Example 3] Preparation of KNK005 lacUV5-phaJ4b/Δpha Z1,2,6 Strain

At the outset, a plasmid used for promoter and SD sequence insertion was prepared in the manner described below.

PCR was carried out under the same conditions as with Production Example 1 using chromosome DNA of the *C. necator* 1-116 strain as a template and the primers as shown by SEQ ID NO: 13 and SEQ ID NO: 14. Also, PCR was carried out under the same conditions using the primers as shown by SEQ ID NO: 15 and SEQ ID NO: 16. Further, PCR was carried out under the same conditions using chromosome DNA of the *E. coli* HB101 strain as a template and the primers as shown by SEQ ID NO: 19 and SEQ ID NO: 20. PCR was carried out under the same conditions using the three types of DNA fragments obtained by the PCR described above as templates and the primers as shown by SEQ ID NO: 13 and SEQ ID NO: 16. The resulting DNA fragment was digested with the restriction enzyme SwaI. The DNA fragment was ligated to the pNS2X-sacB vector (described in JP 2007-259708 A) digested with SwaI with the aid of a DNA ligase (Ligation High; manufactured by Toyobo Co., Ltd.). Thus, a plasmid vector for DNA insertion comprising the nucleotide sequence upstream of the phaJ4b structural gene, the lacUV5 promoter, the phaC1 SD sequence, and phaJ4b structural gene sequence was prepared (i.e., pNS2X-sacB+phaJ4bU-lacUV5-phaJ4b).

Subsequently, a strain with inserted promoter and SD sequence was prepared.

The *E. coli* S17-1 strain (ATCC47055) was transformed with the plasmid vector for promoter and SD sequence insertion (pNS2X-sacB+phaJ4bU-lacUV5-phaJ4b), and the transformed strain was subjected to mixed culture with the KNK005Δpha Z1,2,6 strain prepared in Production Example 1 in a nutrient agar medium (manufactured by Difco) to perform conjugal transfer. The culture was seeded on the Simmons' agar medium containing 250 mg/l kanamycin (2 g/l sodium citrate, 5 g/l sodium chloride, 0.2 g/l magnesium sulfate.7H$_2$O, 1 g/l ammonium dihydrogenphosphate, 1 g/l dipotassium hydrogenphosphate, 15 g/l agar, pH 6.8), strains grown on the agar medium were selected, and the strains comprising the plasmid incorporated into the chromosome of the KNK005Δpha Z1,2,6 strain were obtained. The strains were cultured in the nutrient broth medium (manufactured by Difco) over two generations, the cultured strains were diluted and applied to a 15% sucrose-containing nutrient agar medium, and the grown strains were obtained as strains from which the plasmid had been removed. PCR analysis was further conducted to isolate a strain comprising a DNA fragment as shown by SEQ ID NO: 39 comprising the lacUV5 promoter and the phaC1 SD sequence inserted at a site upstream of the phaJ4b structural gene on the chromosome.

This strain with inserted promoter and SD sequence was designated as the KNK005 lacUV5-phaJ4b/Δpha Z1,2,6 strain.

[Production Example 4] Preparation of KNK005 trp-phaJ4b/Δpha Z1,2,6 Strain

At the outset, a plasmid used for promoter and SD sequence insertion was prepared in the manner described below.

PCR was carried out under the same conditions as with Production Example 1 using chromosome DNA of the *C. necator* H16 strain as a template and the primers as shown by SEQ ID NO: 13 and SEQ ID NO: 14. Also, PCR was carried out under the same conditions using the primers as shown by SEQ ID NO: 15 and SEQ ID NO: 16. Further, PCR was carried out under the same conditions using the pKK388-1 plasmid (manufactured by Clontech Laboratories, Inc.) as a template and the primers as shown by SEQ ID NO: 17 and SEQ ID NO: 21.

PCR was carried out under the same conditions using the three types of DNA fragments obtained by the PCR described above as templates and the primers as shown by SEQ ID NO: 13 and SEQ ID NO: 16. The resulting DNA fragment was digested with the restriction enzyme SwaI. The DNA fragment was ligated to the pNS2X-sacB vector (described in JP 2007-259708 A) digested with SwaI with the aid of a DNA ligase (Ligation High; manufactured by Toyobo Co., Ltd.). Thus, a plasmid vector for DNA insertion comprising the nucleotide sequence upstream of the phaJ4b structural gene, the trp promoter, the phaC1 SD sequence, and the phaJ4b structural gene sequence was prepared (i.e., pNS2X-sacB-+phaJ4bU-trp-phaJ4b).

Subsequently, a strain with inserted promoter and SD sequence was prepared.

The *E. coli* S17-1 strain (ATCC47055) was transformed with the plasmid vector for promoter and SD sequence insertion (pNS2X-sacB+phaJ4bU-trp-phaJ4b), and the transformed strain was subjected to mixed culture with the KNK005Δpha Z1,2,6 strain prepared in Production Example 1 in a nutrient agar medium (manufactured by Difco) to perform conjugal transfer. The culture was seeded on the Simmons' agar medium containing 250 mg/l kanamycin (2 g/l sodium citrate, 5 g/l sodium chloride, 0.2 g/l magnesium sulfate.7H$_2$O, 1 g/l ammonium dihydrogenphosphate, 1 g/l dipotassium hydrogenphosphate, 15 g/l agar, pH 6.8), the strains grown on the agar medium were selected, and the strains comprising the plasmid incorporated into the chromosome of the KNK005Δpha Z1,2,6 strain were obtained. The strains were cultured in the nutrient broth medium (manufactured by Difco) over two generations, the cultured strains were diluted and applied to a 15% sucrose-containing nutrient agar medium, and the grown strains were obtained as strains from which the plasmid had been removed. PCR analysis was further conducted to isolate a strain comprising a DNA fragment as shown by SEQ ID NO: 40 comprising the trp promoter and the phaC1 SD sequence inserted at a site upstream of the phaJ4b structural gene on the chromosome.

This strain with inserted promoter and SD sequence was designated as the KNK005 trp-phaJ4b/Δpha Z1,2,6 strain.

[Production Example 5] Preparation of KNK005 REP-phaJ4b/Δpha Z1,2,6 Strain

At the outset, a plasmid used for promoter and SD sequence insertion was prepared in the manner described below.

PCR was carried out under the same conditions as with Production Example 1 using chromosome DNA of the *C. necator* H16 strain as a template and the primers as shown by SEQ ID NO: 13 and SEQ ID NO: 14. Also, PCR was carried out under the same conditions using the primers as shown by SEQ ID NO: 15 and SEQ ID NO: 16. Also, PCR was carried out under the same conditions using the primers as shown by SEQ ID NO: 22 and SEQ ID NO: 23. PCR was carried out under the same conditions using the three types of DNA fragments obtained by the PCR described above as templates and the primers as shown by SEQ ID NO: 13 and SEQ ID NO: 16. The resulting DNA fragment was digested with the restriction enzyme SwaI. The DNA fragment was ligated to the pNS2X-sacB vector (described in JP 2007-259708 A) digested with SwaI with the aid of a DNA ligase (Ligation High; manufactured by Toyobo Co., Ltd.). Thus, a plasmid vector for DNA insertion comprising the nucleotide sequence upstream of the phaJ4b structural gene, the phaC1 promoter, the phaC1 SD sequence, and the phaJ4b structural gene sequence was prepared (i.e., pNS2X-sacB+phaJ4bU-REP-phaJ4b).

Subsequently, a strain with inserted promoter and SD sequence was prepared.

The *E. coli* S17-1 strain (ATCC47055) was transformed with the plasmid vector for promoter and SD sequence insertion (pNS2X-sacB+phaJ4bU-REP-phaJ4b), and the transformed strain was subjected to mixed culture with the KNK005Δpha Z1,2,6 strain prepared in Production Example 1 in a nutrient agar medium (manufactured by Difco) to perform conjugal transfer. The culture was seeded on the Simmons' agar medium containing 250 mg/l kanamycin (2 g/l sodium citrate, 5 g/l sodium chloride, 0.2 g/l magnesium sulfate.7H$_2$O, 1 g/l ammonium dihydrogenphosphate, 1 g/l potassium hydrogenphosphate, 15 g/l agar, pH 6.8), the strains grown on the agar medium were selected, and the strains comprising the plasmid incorporated into the chromosome of the KNK005Δpha Z1,2,6 strain were obtained. The strains were cultured in the nutrient broth medium (manufactured by Difco) over two generations, the cultured strains were diluted and applied to a 15% sucrose-containing nutrient agar medium, and the grown strains were obtained as strains from which the plasmid had been removed. PCR analysis was further conducted to isolate a strain comprising a DNA fragment as shown by SEQ ID NO: 37 comprising the phaC1 promoter and the phaC1 SD sequence inserted at a site upstream of the phaJ4b structural gene on the chromosome.

This strain with inserted promoter and SD sequence was designated as the KNK005 REP-phaJ4b/Δpha Z1,2,6 strain.

[Production Example 6] Preparation of KNK005 REPSDM11-phaJ4b/Δpha Z1,2,6 Strain

At the outset, a plasmid used for promoter and SD sequence insertion was prepared in the manner described below.

PCR was carried out under the same conditions as with Production Example 1 using chromosome DNA of the *C. necator* H16 strain as a template and the primers as shown by SEQ ID NO: 13 and SEQ ID NO: 14. Also, PCR was carried out under the same conditions using the primers as shown by SEQ ID NO: 24 and SEQ ID NO: 16. Also, PCR was carried out under the same conditions using the primers as shown by SEQ ID NO: 22 and SEQ ID NO: 25.

PCR was carried out under the same conditions using the three types of DNA fragments obtained by the PCR described above as templates and the primers as shown by SEQ ID NO: 13 and SEQ ID NO: 16. The resulting DNA fragment was digested with the restriction enzyme SwaI. The DNA fragment was ligated to the pNS2X-sacB vector (described in JP 2007-259708 A) digested with SwaI with the aid of a DNA ligase (Ligation High; manufactured by Toyobo Co., Ltd.). Thus, a plasmid vector for DNA insertion comprising the nucleotide sequence upstream of the phaJ4b structural gene, the phaC1 promoter, a modified phaC1 SD sequence, and the phaJ4b structural gene sequence was prepared (i.e., pNS2X-sacB+phaJ4bU-REPSDM11-phaJ4b).

Subsequently, a strain with inserted promoter and SD sequence was prepared.

The *E. coli* S17-1 strain (ATCC47055) was transformed with the plasmid vector for promoter and SD sequence insertion (pNS2X-sacB+phaJ4bU-REPSDM11-phaJ4b), and the transformed strain was subjected to mixed culture with the KNK005Δpha Z1,2,6 strain prepared in Production Example 1 in a nutrient agar medium (manufactured by Difco) to perform conjugal transfer. The culture solution was seeded on the Simmons' agar medium containing 250 mg/l kanamycin (2 g/l sodium citrate, 5 g/l sodium chloride, 0.2 g/l magnesium sulfate.7H$_2$O, 1 g/l ammonium dihydrogenphosphate, 1 g/l dipotassium hydrogenphosphate, 15 g/l agar, pH 6.8), the strains grown on the agar medium were selected, and the strains comprising the plasmid incorporated into the chromosome of the KNK005Δpha Z1,2,6 strain were obtained. The strains were cultured in the nutrient broth medium (manufactured by Difco) over two generations, the cultured strains were diluted and applied to a 15% sucrose-containing nutrient agar medium, and the grown strains were obtained as strains from which the plasmid had been removed. PCR analysis was further conducted to isolate a strain comprising a DNA fragment comprising the phaC1 promoter and a modified phaC1 SD sequence inserted at a site upstream of the phaJ4b structural gene on the chromosome as shown by SEQ ID NO: 41.

This strain with inserted promoter and SD sequence was designated as the KNK005 REPSDM11-phaJ4b/Δpha Z1,2,6 strain.

[Production Example 7] Preparation of KNK005 REPN17SDM11-phaJ4b/Δpha Z1,2,6 Strain At the outset, a plasmid used for promoter and SD sequence insertion was prepared in the manner described below.

PCR was carried out under the same conditions as with Production Example 1 using the plasmid vector prepared in Production Example 6 (pNS2X-sacB+phaJ4bU-REPSDM11-phaJ4b) as a template and the primers as shown by SEQ ID NO: 13 and SEQ ID NO: 26. Also, PCR was carried out under the same conditions using the primers as shown by SEQ ID NO: 27 and SEQ ID NO: 16. PCR was carried out under the same conditions using the two types of DNA fragments obtained by the PCR described above as templates and the primers as shown by SEQ ID NO: 13 and SEQ ID NO: 16. The resulting DNA fragment was digested with the restriction enzyme SwaI. The DNA fragment was ligated to the pNS2X-sacB vector (described in JP 2007-259708 A) digested with SwaI with the aid of a DNA ligase (Ligation High; manufactured by Toyobo Co., Ltd.). Thus, a plasmid vector for DNA insertion comprising the nucleotide sequence upstream of the phaJ4b structural gene, a modified phaC1 promoter, a modified phaC1 SD sequence, and the phaJ4b structural gene sequence was prepared (i.e., pNS2X-sacB-+phaJ4bU-REPN17SDM11-phaJ4b).

Subsequently, a strain with inserted promoter and SD sequence was prepared.

The *E. coli* S17-1 strain (ATCC47055) was transformed with the plasmid vector for promoter and SD sequence insertion (pNS2X-sacB+phaJ4bU-REPN17SDM11-phaJ4b), and the transformed strain was subjected to mixed culture with the KNK005Δpha Z1,2,6 strain prepared in Production Example 1 in a nutrient agar medium (manufactured by Difco) to perform conjugal transfer. The culture was seeded on the Simmons' agar medium containing 250 mg/l kanamycin (2 g/l sodium citrate, 5 sodium chloride, 0.2 g/l magnesium sulfate.7H$_2$O, 1 g/l ammonium dihydrogenphosphate, 1 g/l dipotassium hydrogenphosphate, 15 g/l agar, pH 6.8), the strains grown on the agar medium were selected, and the strains comprising the plasmid incorporated into the chromosome of the KNK005Δpha Z1,2,6 strain were obtained. The strains were cultured in the nutrient broth medium (manufactured by Difco) over two generations, the cultured strains were diluted and applied to a 15% sucrose-containing nutrient agar medium, and the grown strains were obtained as strains from which the plasmid had been removed. PCR analysis was further conducted to isolate a strain comprising a DNA fragment as shown by SEQ ID NO: 42 comprising a modified phaC1 promoter and a modified phaC1 SD sequence inserted at a site upstream of the phaJ4b structural gene on the chromosome.

This strain with inserted promoter and SD sequence was designated as the KNK005 REPN17SDM11-phaJ4b/Δpha Z1,2,6 strain.

[Production Example 8] Preparation of KNK005 trcSDM11-phaJ4a/Δpha Z1,2,6 Strain

At the outset, a plasmid used for promoter and SD sequence insertion was prepared in the manner described below.

PCR was carried out under the same conditions as with Production Example 1 using chromosome DNA of the *C. necator* H16 strain as a template and the primers as shown by SEQ ID NO: 28 and SEQ ID NO: 29. Also, PCR was carried out under the same conditions using the primers as shown by SEQ ID NO: 30 and SEQ ID NO: 31. Further, PCR was carried out under the same conditions using the pKK388-1 plasmid (manufactured by Clontech Laboratories, Inc.) as a template and the primers as shown by SEQ ID NO: 32 and SEQ ID NO: 33.

PCR was carried out under the same conditions using the three types of DNA fragments obtained by the PCR described above as templates and the primers as shown by SEQ ID NO: 28 and SEQ ID NO: 31. The resulting DNA fragment was digested with the restriction enzyme SwaI. The DNA fragment was ligated to the pNS2X-sacB vector (described in JP 2007-259708 A) digested with SwaI with the aid of a DNA ligase (Ligation High; manufactured by Toyobo Co., Ltd.). Thus, a plasmid vector for DNA insertion comprising the nucleotide sequence upstream of the phaJ4a structural gene, the trc promoter, a modified phaC1 SD sequence, and the phaJ4a structural gene sequence was prepared (i.e., pNS2X-sacB+phaJ4aU-trcSDM11-phaJ4a).

Subsequently, a strain with inserted promoter and SD sequence was prepared.

The *E. coli* S17-1 strain (ATCC47055) was transformed with the plasmid vector for promoter and SD sequence insertion (pNS2X-sacB+phaJ4aU-trcSDM11-phaJ4a), and the transformed strain was subjected to mixed culture with the KNK005Δpha Z1,2,6 strain prepared in Production Example 1 in a nutrient agar medium (manufactured by Difco) to perform conjugal transfer. The culture was seeded on the Simmons' agar medium containing 250 mg/l kanamycin (2 g/l sodium citrate, 5 g/l sodium chloride, 0.2 g/l magnesium sulfate 7H$_2$O, 1 g/l ammonium dihydrogenphosphate, 1 g/l dipotassium hydrogenphosphate, 15 g/l agar, pH 6.8), the strains grown on the agar medium were selected, and the strains comprising the plasmid incorporated into the chromosome of the KNK005Δpha Z1,2,6 strain were obtained. The strains were cultured in the nutrient broth medium (manufactured by Difco) over two generations, the cultured strains were diluted and applied to a 15% sucrose-containing nutrient agar medium, and the grown strains were obtained as strains from which the plasmid had been removed. PCR analysis was further conducted to isolate a strain comprising a DNA fragment as shown by SEQ ID NO: 43 comprising the trc promoter and the modified phaC1 SD sequence at a site upstream of the phaJ4a structural gene on the chromosome.

This strain with inserted promoter and SD sequence was designated as the KNK005 trcSDM11-phaJ4a/Δpha Z1,2,6 strain.

[Production Example 9] Preparation of KNK005 lacUV5-phaJ4a/Δpha Z1,2,6 Strain

At the outset, a plasmid used for promoter and SD sequence insertion was prepared in the manner described below.

PCR was carried out under the same conditions as with Production Example 1 using chromosome DNA of the *C. necator* H16 strain as a template and the primers as shown by SEQ ID NO: 28 and SEQ ID NO: 29. Also, PCR was carried out under the same conditions using the primers as shown by SEQ ID NO: 34 and SEQ ID NO: 31. Further, PCR was carried out under the same conditions using chromosome DNA of the *E. coli* HB101 strain as a template and the primers as shown by SEQ ID NO: 35 and SEQ ID NO: 20. PCR was carried out under the same conditions using the three types of DNA fragments obtained as a result of the PCR procedures described above as templates and the primers as shown by SEQ ID NO: 28 and SEQ ID NO: 31. The resulting DNA fragment was digested with the restriction enzyme SwaI. The DNA fragment was ligated to the pNS2X-sacB vector (described in JP 2007-259708 A) digested with SwaI with the aid of a DNA ligase (Ligation High; manufactured by Toyobo Co., Ltd.). Thus, a plasmid vector for DNA insertion comprising the nucleotide sequence upstream of the phaJ4a structural gene, the lacUV5 promoter, the phaC1 SD sequence, and the phaJ4a structural gene sequence was prepared (i.e., pNS2X-sacB+phaJ4aU-lacUV5-phaJ4a).

Subsequently, a strain with inserted promoter and SD sequence was prepared.

The *E. coli* S17-1 strain (ATCC47055) was transformed with the plasmid vector for promoter and SD sequence insertion (pNS2X-sacB+phaJ4aU-lacUV5-phaJ4a), and the transformed strain was subjected to mixed culture with the KNK005Δpha Z1,2,6 strain prepared in Production Example 1 in a nutrient agar medium (manufactured by Difco) to perform conjugal transfer. The culture was seeded on the Simmons' agar medium containing 250 mg/l kanamycin (2 g/l sodium citrate, 5 g/l sodium chloride, 0.2 g/l magnesium sulfate.7H$_2$O, 1 g/l ammonium dihydrogenphosphate, 1 g/l dipotassium hydrogenphosphate, 15 g/l agar, pH 6.8), the strains grown on the agar medium were selected, and the strains comprising the plasmid incorporated into the chromosome of the KNK005Δpha Z1,2,6 strain were obtained. The strains were cultured in the nutrient broth medium (manufactured by Difco) over two generations, the cultured strains were diluted and applied to a 15% sucrose-containing nutrient agar medium, and the grown strains were obtained as strains from which the plasmid had been removed. PCR analysis was further conducted to isolate a strain comprising a DNA fragment as shown by SEQ ID NO: 39 comprising the lacUV5 promoter and the phaC1 SD sequence inserted into a site upstream of the phaJ4a structural gene on the chromosome.

This strain with inserted promoter and SD sequence was designated as the KNK005 lacUV5-phaJ4a/Δpha Z1,2,6 strain.

[Production Example 10] Preparation of KNK005 lacUV5SDM11-phaJ4a/Δpha Z1,2,6 Strain At the outset, a plasmid used for promoter and SD sequence insertion was prepared in the manner described below.

PCR was carried out under the same conditions as with Production Example 1 using the plasmid vector prepared in Production Example 9 (pNS2X-sacB+phaJ4aU-lacUV5-phaJ4a) as a template and the primers as shown by SEQ ID NO: 28 and SEQ ID NO: 33. Also, PCR was carried out under the same conditions using the primers as shown by SEQ ID NO: 30 and SEQ ID NO: 31. PCR was carried out under the same conditions using the two types of DNA fragments obtained as a result of the PCR procedures described above as templates and the primers as shown by SEQ ID NO: 28 and SEQ ID NO: 31. The resulting DNA fragment was digested with the restriction enzyme SwaI. The DNA fragment was ligated to the pNS2X-sacB vector (described in JP 2007-259708 A) digested with SwaI with the aid of a DNA ligase (Ligation High; manufactured by Toyobo Co., Ltd.). Thus, a plasmid vector for DNA insertion comprising the nucleotide sequence upstream of the phaJ4a structural gene, the lacUV5 promoter, a modified phaC1 SD sequence, and the phaJ4a structural gene sequence was prepared (i.e., pNS2X-sacB+phaJ4aU-lacUV5SDM11-phaJ4a).

Subsequently, a strain with inserted promoter and SD sequence was prepared.

The *E. coli* S17-1 strain (ATCC47055) was transformed with the plasmid vector for promoter and SD sequence insertion (pNS2X-sacB+phaJ4aU-lacUV5SDM11-phaJ4a), and the transformed strain was subjected to mixed culture with the KNK005Δpha Z1,2,6 strain prepared in Production Example 1 in a nutrient agar medium (manufactured by Difco) to perform conjugal transfer. The culture was seeded on the Simmons' agar medium containing 250 mg/l kanamycin (2 g/l sodium citrate, 5 g/l sodium chloride, 0.2 WI magnesium sulfate.7H$_2$O, 1 g/l ammonium dihydrogenphosphate, 1 g/l dipotassium hydrogenphosphate, 15 g/l agar, pH 6.8), the strains grown on the agar medium were selected, and the strains comprising the plasmid incorporated into the chromosome of the KNK005Δpha Z1,2,6 strain were obtained. The strains were cultured in the nutrient broth medium (manufactured by Difco) over two generations, the cultured strains were diluted and applied to a 15% sucrose-containing nutrient agar medium, and the grown strains were obtained as strains from which the plasmid had been removed. PCR analysis was further conducted to isolate a strain comprising a DNA fragment as shown by SEQ ID NO: 44 comprising the lacUV5 promoter and the modified phaC1 SD sequence inserted at a site upstream of the phaJ4a structural gene on the chromosome.

This strain with inserted promoter and SD sequence was designated as the KNK005 lacUV5SDM11-phaJ4a/Δpha Z1,2,6 strain.

[Production Example 11] Preparation of KNK005 trp-phaJ4a/Δpha Z1,2,6 Strain

At the outset, a plasmid used for promoter and SD sequence insertion was prepared in the manner described below.

PCR was carried out under the same conditions as with Production Example 1 using chromosome DNA of the *C. necator* H16 strain as a template and the primers as shown by SEQ ID NO: 28 and SEQ ID NO: 29. Also, PCR was carried out under the same conditions using the primers as shown by SEQ ID NO: 34 and SEQ ID NO: 31. Further, PCR was carried out under the same conditions using the pKK388-1 plasmid (manufactured by Clontech Laboratories, Inc.) as a template and the primers as shown by SEQ ID NO: 32 and SEQ ID NO: 21, PCR was carried out under the same conditions using the three types of DNA fragments obtained by the PCR described above as templates and the primers as shown by SEQ ID NO: 28 and SEQ ID NO: 31. The resulting DNA fragment was digested with the restriction enzyme SwaI. The DNA fragment was ligated to the pNS2X-sacB vector (described in JP 2007-259708 A) digested with SwaI with the aid of a DNA ligase (Ligation High; manufactured by Toyobo Co., Ltd.). Thus, a plasmid vector for DNA insertion comprising the nucleotide sequence upstream of the phaJ4a structural gene, the tip promoter, the phaC1 SD sequence, and the phaJ4a structural gene sequence was prepared (i.e., pNS2X-sacB+phaJ4aU-trp-phaJ4a).

Subsequently, a strain with inserted promoter and SD sequence was prepared.

The *E. coli* S17-1 strain (ATCC47055) was transformed with the plasmid vector for promoter and SD sequence insertion (pNS2X-sacB+phaJ4aU-trp-phaJ4a), and the transformed strain was subjected to mixed culture with the KNK005Δpha Z1,2,6 strain prepared in Production Example 1 in a nutrient agar medium (manufactured by Difco) to perform conjugal transfer. The culture was seeded on the Simmons' agar medium containing 250 mg/l kanamycin (2 g/l sodium citrate, 5 g/l sodium chloride, 0.2 g/l magnesium sulfate.7H$_2$O, 1 g/l ammonium dihydrogenphosphate, 1 g/l dipotassium hydrogenphosphate, 15 g/l agar, pH 6.8), the strains grown on the agar medium were selected, and the strains comprising the plasmid incorporated into the chromosome of the KNK005Δpha Z1,2,6 strain were obtained. The strains were cultured in the nutrient broth medium (manufactured by Difco) over two generations, the cultured strains were diluted and applied to a 15% sucrose-containing nutrient agar medium, and the grown strains were obtained as strains from which the plasmid had been removed. PCR analysis was further conducted to isolate a strain comprising a DNA fragment as shown by SEQ ID NO: 40 comprising the trp promoter and the phaC1 SD sequence inserted at a site upstream of the phaJ4a structural gene on the chromosome.

This strain with inserted promoter and SD sequence was designated as the KNK005 trp-phaJ4a/Δpha Z1,2,6 strain.

[Production Example 12] Preparation of KNK005 trpSDM11-phaJ4a/Δpha Z1,2,6 Strain At the outset, a plasmid used for promoter and SD sequence insertion was prepared in the manner described below.

PCR was carried out under the same conditions as with Production Example 1 using the plasmid vector prepared in Production Example 11 (pNS2X-sacB-+phaJ4aU-trp-phaJ4a) as a template and the primers as shown by SEQ ID NO: 28 and SEQ ID NO: 33. Also, PCR was carried out under the same conditions using the primers as shown by SEQ ID NO: 30 and SEQ ID NO: 31, PCR was carried out under the same conditions using the two types of DNA fragments obtained by the PCR described above as templates and the primers as shown by SEQ ID NO: 28 and SEQ ID NO: 31. The resulting DNA fragment was digested with the restriction enzyme SwaI. The DNA fragment was ligated to the pNS2X-sacB vector (described in JP 2007-259708 A) digested with SwaI with the aid of a DNA ligase (Ligation High; manufactured by Toyobo Co., Ltd.). Thus, a plasmid vector for DNA insertion comprising the nucleotide sequence upstream of the phaJ4a structural gene, the trp promoter, a modified phaC1 SD sequence, and the phaJ4a structural gene sequence was prepared (i.e., pNS2X-sacB-f-phaJ4aU-trpSDM11-phaJ4a).

Subsequently, a strain with inserted promoter and SD sequence was prepared.

The *E. coli* S17-1 strain (ATCC47055) was transformed with the plasmid vector for promoter and SD sequence insertion (pNS2X-sacB+phaJ4aU-trp SDM11-phaJ4a), and the transformed strain was subjected to mixed culture with the KNK005Δpha Z1,2,6 strain prepared in Production Example 1 in a nutrient agar medium (manufactured by Difco) to perform conjugal transfer. The culture solution was seeded on the Simmons' agar medium containing 250 mg/l kanamycin (2 sodium citrate, 5 g/l sodium chloride, 0.2 g/l magnesium sulfate.$7H_2O$, 1 g/l ammonium dihydrogenphosphate, 1 g/l dipotassium hydrogenphosphate, 15 g/l agar, pH 6.8), the strains grown on the agar medium were selected, and the strains comprising the plasmid incorporated into the chromosome of the KNK005Δpha Z1,2,6 strain were obtained. The strains were cultured in the nutrient broth medium (manufactured by Difco) over two generations, the cultured strains were diluted and applied to a 15% sucrose-containing nutrient agar medium, and the grown strains were obtained as strains from which the plasmid had been removed. PCR analysis was further conducted to isolate a strain comprising a DNA fragment as shown by SEQ ID NO: 45 comprising the trp promoter and the modified phaC1 SD sequence inserted into a site upstream of the phaJ4a structural gene on the chromosome.

This strain with inserted promoter and SD sequence was designated as the KNK005 trpSDM11-phaJ4a/Δpha Z1,2,6 strain.

[Production Example 13] Preparation of KNK005 REP-phaJ4a/Δpha Z1,2,6 Strain

At the outset, a plasmid used for promoter and SD sequence insertion was prepared in the manner described below.

PCR was carried out under the same conditions as with Production Example 1 using chromosome DNA of the *C. necator* H16 strain as a template and the primers as shown by SEQ ID NO: 28 and SEQ ID NO: 29. Also, PCR was carried out under the same conditions using the primers as shown by SEQ ID NO: 34 and SEQ ID NO: 31. Further, PCR was carried out under the same conditions using the primers as shown by SEQ ID NO: 36 and SEQ ID NO: 23. In addition, PCR was carried out under the same conditions using the three types of DNA fragments obtained by the PCR described above as templates and the primers as shown by SEQ ID NO: 28 and SEQ ID NO: 31. The resulting DNA fragment was digested with the restriction enzyme SwaI. The DNA fragment was ligated to the pNS2X-sacB vector (described in JP 2007-259708 A) digested with SwaI with the aid of a DNA ligase (Ligation High; manufactured by Toyobo Co., Ltd.).

Thus, a plasmid vector for DNA insertion comprising the nucleotide sequence upstream of the phaJ4a structural gene, the phaC1 promoter, the phaC1 SD sequence, and the phaJ4a structural gene sequence was prepared (i.e., pNS2X-sacB+phaJ4aU-REP-phaJ4a).

Subsequently, a strain with inserted promoter and SD sequence was prepared.

The *E. coli* S17-1 strain (ATCC47055) was transformed with the plasmid vector for promoter and SD sequence insertion (pNS2X-sacB-+phaJ4aU-REP-phaJ4a), and the transformed strain was subjected to mixed culture with the KNK005Δpha Z1,2,6 strain prepared in Production Example 1 in a nutrient agar medium (manufactured by Difco) to perform conjugal transfer. The culture solution was seeded on the Simmons' agar medium containing 250 mg/l kanamycin (2 WI sodium citrate, 5 g/l sodium chloride, 0.2 magnesium sulfate.$7H_2O$, 1 ammonium dihydrogenphosphate, 1 g/l dipotassium hydrogenphosphate, 15 g/l agar, pH 6.8), the strains grown on the agar medium were selected, and the strains comprising the plasmid incorporated into the chromosome of the KNK005Δpha Z1,2,6 strain were obtained. The strains were cultured in the nutrient broth medium (manufactured by Difco) over two generations, the cultured strains were diluted and applied to a 15% sucrose-containing nutrient agar medium, and the grown strains were obtained as strains from which the plasmid had been removed. PCR analysis was further conducted to isolate a strain comprising a DNA fragment as shown by SEQ ID NO: 37 comprising the phaC1 promoter and the phaC1 SD sequence inserted at a site upstream of the phaJ4a structural gene on the chromosome.

This strain with inserted promoter and SD sequence was designated as the KNK005 REP-phaJ4a/Δpha Z1,2,6 strain.

[Example 1] Production of PHA by KNK005 trc-phaJ4b/Δpha Z1,2,6 Strain

The seed culture medium was composed of 1 w/v % meat extract, 1 w/v % Bacto tryptone, 0.2 w/v % yeast extract, 0.9 w/v % $Na_2HPO_4.12H_2O$, and 0.15 w/v % $KH_2PO_4$.

The PHA production medium was composed of 1.1 w/v % $Na_2HPO_4.12H_2O$, 0.19 w/v % $KH_2PO_4$, 0.13 w/v % $(NH_4)_2SO_4$, 0.1 w/v % $MgSO_4.7H_2O$, and a 0.1 v/v % trace metal salt solution (1.6 w/v % $FeCl_3.6H_2O$, 1 w/v % $CaCl_2.2H_2O$, 0.02 w/v % $CoCl_2.6H_2O$, 0.016 w/v % $CuSO_4.5H_2O$, and 0.012 w/v % $NiCl_2.6H_2O$ dissolved in 0.1 N hydrochloric acid). Palm kernel olein, which is a low-melting fraction separated from palm kernel oil, was used as a single carbon source.

A glycerol stock (50 μl) of the KNK005 trc-phaJ4b/Δpha Z1,2,6 strain prepared in Production Example 2 was inoculated into the seed culture medium (10 ml), and culture was conducted for 24 hours to obtain a seed culture liquid. At the time of culture for PHA production, the seed culture liquid was inoculated at 1.0 v/v % into a Sakaguchi flask containing 50 ml of the production medium. Shake culture was conducted at 30° C. for 72 hours. After the completion of culture, cells were recovered via centrifugation, washed with methanol, and freeze-dried. The weight of dry cells was then measured.

Chloroform (100 ml) was added to 1 g of the dry cells thus obtained, the mixture was stirred at room temperature during a whole day and night, and PHAs were then extracted from the cells. After the residue of the cells was separated via filtration, the extract was concentrated to bring the total volume to 30 ml with an evaporator, 90 ml hexane was gradually added thereto, and the mixture was then allowed to stand for 1 hour with slow stirring. The precipitated PHA was separated via filtration and then vacuum dried at 50° C. for 3 hours. The weight of the dry PHA was measured, and the amount of PHA produced was determined. The results are shown in Table 1.

TABLE 1

| Strain | | Amount of PHA production (g/l) | 3HH composition ratio (mol %) |
|---|---|---|---|
| Example 1 | KNK005 trc-phaJ4b/ΔphaZ1,2,6 | 16.6 | 10.91 |
| Example 2 | KNK005 lacUV5-phaJ4b/ΔphaZ1,2,6 | 14.7 | 11.65 |
| Example 3 | KNK005 trp-phaJ4b/ΔphaZ1,2,6 | 16.3 | 10.49 |
| Example 4 | KNK005 REP-phaJ4b/ΔphaZ1,2,6 | 16.5 | 7.46 |
| Example 5 | KNK005 REPSDM11-phaJ4b/ΔphaZ1,2,6 | 16.3 | 6.56 |
| Example 6 | KNK005 REPN17SDM11-phaJ4b/ΔphaZ1,2,6 | 15.1 | 6.19 |
| Example 7 | KNK005 trcSDM11-phaJ4a/ΔphaZ1,2,6 | 18.4 | 10.70 |
| Example 8 | KNK005 lacUV5-phaJ4a/ΔphaZ1,2,6 | 16.8 | 10.57 |
| Example 9 | KNK005 lacUV5SDM11-phaJ4a/ΔphaZ1,2,6 | 18.2 | 9.85 |
| Example 10 | KNK005 trp-phaJ4a/ΔphaZ1,2,6 | 17.8 | 9.48 |
| Example 11 | KNK005 trpSDM11-phaJ4a/ΔphaZ1,2,6 | 17.1 | 8.51 |
| Example 12 | KNK005 REP-phaJ4a/ΔphaZ1,2,6 | 15.9 | 6.06 |
| Comparative Example 1 | KNK005ΔphaZ1,2,6 | 18.3 | 3.88 |

The 3HH composition ratio of the produced polyester was analyzed via gas chromatography in the manner described below. 2 ml of sulfuric acid-methanol (15:85) mixture and 2 ml of chloroform were added to about 20 mg of dry polyester. The system was tightly stoppered and heated at 100° C. for 140 minutes to afford methyl esters which are polyester degradation products. After cooling, 1.5 g of sodium bicarbonate was gradually added to neutralize the mixture, and the resultant was allowed to stand until generation of carbon dioxide gas ceased. Diisopropyl ether (4 ml) was added, and the mixture was thoroughly mixed, followed by centrifugation. The monomer unit composition of the polyester degradation products in the supernatant was analyzed by capillary gas chromatography using the gas chromatograph (GC-17A, manufactured by Shimadzu Corporation) and the capillary column (NEUTRA BOND-4, manufactured by GL Sciences Inc., column length: 25 m, column internal diameter: 0.25 mm, liquid film thickness: 0.4 μm). He carrier gas was used, a column inlet pressure was 100 kPa, and 1 μl of the sample was injected thereinto. The temperature conditions involved: an initial temperature of 100° C.; temperature elevation from 100° C. to 200° C. at a rate of 8° C./min; and additional temperature elevation from 200° C. to 290° C. at a rate of 30° C./min.

As a result of analysis conducted under the aforementioned conditions, the polyester obtained was found to be a polyester copolymer (i.e., P(3HB-co-3HH)), and the 3HH composition ratio was as shown by Table 1 above.

[Example 2] Production of PHA by KNK005 lacUV5-phaJ4b/Δpha Z1,2,6 Strain

Using the KNK005 lacUV5-phaJ4b/Δpha Z1,2,6 strain produced in Production Example 3 instead of the KNK005 trc-phaJ4b/Δpha Z1,2,6 strain, PHA was produced in the same manner as in Example 1, and the amount of the produced PHA and the 3HH composition ratio were measured. The results are shown in Table 1 above.

[Example 3] Production of PHA by KNK005 trp-phaJ4b/Δpha Z1,2,6 Strain

Using the KNK005 trp-phaJ4b/Δpha Z1,2,6 strain produced in Production Example 4 instead of the KNK005 trc-phaJ4b/Δpha Z1,2,6 strain, PHA was produced in the same manner as in Example 1, and the amount of the produced PHA and the 3HH composition ratio were measured. The results are shown in Table 1 above.

[Example 4] Production of PHA by KNK005 REP-phaJ4b/Δpha Z1,2,6 Strain

Using the KNK005 REP-phaJ4b/Δpha Z1,2,6 strain produced in Production Example 5 instead of the KNK005 trc-phaJ4b/Δpha Z1,2,6 strain, PHA was produced in the same manner as in Example 1, and the amount of the produced PHA and the 3HH composition ratio were measured. The results are shown in Table 1 above.

[Example 5] Production of PHA by KNK005 REPSDM11-phaJ4b/Δpha Z1,2,6 Strain

Using the KNK005 REPSDM11-phaJ4b/Δpha Z1,2,6 strain produced in Production Example 6 instead of the KNK005 trc-phaJ4b/Δpha Z1,2,6 strain, PHA was produced in the same manner as in Example 1, and the amount of the produced PHA and the 3HH composition ratio were measured. The results are shown in Table 1 above.

[Example 6] Production of PHA by KNK005 REPN17SDM11-phaJ4b/Δpha Z1,2,6 Strain

Using the KNK005 REPN17SDM11-phaJ4b/Δpha Z1,2,6 strain produced in Production Example 7 instead of the KNK005 trc-phaJ4b/Δpha Z1,2,6 strain, PHA was produced in the same manner as in Example 1, and the amount of the produced PHA and the 3HH composition ratio were measured. The results are shown in Table 1 above.

[Example 7] Production of PHA by KNK005 trcSDM11-phaJ4a/Δpha Z1,2,6 Strain

Using the KNK005 trcSDM11-phaJ4a/Δpha Z1,2,6 strain produced in Production Example 8 instead of the KNK005 trc-phaJ4b/Δpha Z1,2,6 strain, PHA was produced in the same manner as in Example 1, and the amount of the produced PHA and the 3HH composition ratio were measured. The results are shown in Table 1 above.

[Example 8] Production of PHA by KNK005 lacUV5-phaJ4a/Δpha Z1,2,6 Strain

Using the KNK005 lacUV5-phaJ4a/Δpha Z1,2,6 strain produced in Production Example 9 instead of the KNK005 trc-phaJ4b/Δpha Z1,2,6 strain, PHA was produced in the same manner as in Example 1, and the amount of the produced PHA and the 3HH composition ratio were measured. The results are shown in Table 1 above.

[Example 9] Production of PHA by KNK005 lacUV5SDM11-phaJ4a/Δpha Z1,2,6 Strain

Using the KNK005 lacUV5SDM11-phaJ4a/Δpha Z1,2,6 strain produced in Production Example 10 instead of the KNK005 trc-phaJ4b/Δpha Z1,2,6 strain, PHA was produced in the same manner as in Example 1, and the amount of the produced PHA and the 3HH composition ratio were measured. The results are shown in Table 1 above.

[Example 10] Production of PHA by KNK005 trp-phaJ4a/Δpha Z1,2,6 Strain

Using the KNK005 trp-phaJ4a/Δpha Z1,2,6 strain produced in Production Example 11 instead of the KNK005 trc-phaJ4b/Δpha Z1,2,6 strain, PHA was produced in the same manner as in Example 1, and the amount of the produced PHA and the 3HH composition ratio were measured. The results are shown in Table 1 above.

[Example 11] Production of PHA by KNK005 trpSDM11-phaJ4a/Δpha Z1,2,6 strain

Using the KNK005 trpSD11-phaJ4a/Δpha Z1,2,6 strain produced in Production Example 12 instead of the KNK005 trc-phaJ4b/Δpha Z1,2,6 strain, PHA was produced in the same manner as in Example 1, and the amount of the produced PHA and the 3HH composition ratio were measured. The results are shown in Table 1 above.

[Example 12] Production of PHA by KNK005 REP-phaJ4a/Δpha Z1,2,6 Strain

Using the KNK005 REP-phaJ4a/Δpha Z1,2,6 strain produced in Production Example 13 instead of the KNK005 trc-phaJ4b/Δpha Z1,2,6 strain, PHA was produced in the same manner as in Example 1, and the amount of the produced PHA and the 3HH composition ratio were measured.

[Comparative Example 1] Production of PHA by KNK005Δpha Z1,2,6 Strain

Using the KNK005Δpha Z1,2,6 strain produced in Production Example 1 instead of the KNK005 trc-phaJ4b/Δpha Z1,2,6 strain, PHA was produced in the same manner as in Example 1, and the amount of the produced PHA and the 3HH composition ratio were measured. The results are shown in Table 1 above.

[Example 13] Test for Investigation of Influence of Other Expression Regulatory Sequences on Production of PHA by Microorganism Strains and on 3HH Composition Ratio and Results Thereof (13-1) Preparation of the Plasmid Vector pCUP2-REP-phaJ4b A pCUP2-REP-phaJ4b plasmid vector into which DNA comprising the phaC1 wild-type promoter (REP) and SD sequence of the C. necator H16 strain and the nucleotide sequence comprising the phaJ4b gene has been inserted was prepared in the manner described below. PCR was carried out using the chromosome DNA of the C. necator H16 strain as a template and the primers as shown by SEQ ID NO: 72 and SEQ ID NO: 23. A PCR cycle of (1) 98° C. for 2 minutes and (2) 98° C. for 15 seconds, 60° C. for 30 seconds, and 68° C. for 2 minutes was repeated 25 times, and the polymerase KOD-plus—(manufactured by Toyobo Co., Ltd.) was used. The DNA fragment obtained via PCR was designated as REP. Subsequently, PCR was carried out under the same conditions using the chromosome DNA of the C. necator H16 strain as a template and the primers as shown by SEQ ID NO: 70 and SEQ ID NO: 71. The DNA fragment obtained via PCR was designated as (ReSD)-phaJ4b. Subsequently, PCR was carried out under the same conditions using REP and (ReSD)-phaJ4b as templates and the primers as shown by SEQ ID NO: 72 and SEQ ID NO: 71. The DNA fragment obtained via PCR was digested with EcoRI. The resulting DNA fragment was designated as REP-phaJ4b (EcoRI). REP-phaJ4b(EcoRI) was ligated to the plasmid vector pCUP2 disclosed in WO 2007/049716, which had been cleaved with MunI. The nucleotide sequence of the plasmid vector comprising REP-phaJ4b(EcoRI) ligated to pCUP2, which had been cleaved with MunI, was determined using a DNA Sequencer (3130xl Genetic Analyzer, manufactured by Applied BioSystems), such nucleotide sequence was determined to be identical to the nucleotide sequence of the template DNA, and a sequence into which the phaJ4b gene had been inserted in a direction opposite from that of the parP gene on pCUP2 was obtained. The plasmid vector obtained was designated as pCUP2-REP-phaJ4b.

(13-2) Preparation of the Promoter-Modified Plasmid Vector pCUP2-REPP3M14-phaJ4b A mutation as shown by SEQ ID NO: 73 was introduced into the plasmid vector pCUP2-REP-phaJ4b prepared in (13-1) at the phaC1C promoter of the C. necator H16 strain that regulates phaJ4b expression, so as to prepare pCUP2-REPP3M14-phaJ4b in the manner described below.

PCR was carried out under the same conditions as with (13-1) using the pCUP2-REP-phaJ4b plasmid vector prepared in (13-1) as a template and the primers as shown by SEQ ID NO: 72 and SEQ ID NO: 74. The DNA fragment obtained via PCR was designated as REP-PU. Subsequently, PCR was carried out under the same conditions as with (13-1) using the plasmid vector pCUP2-REP-phaJ4b prepared in (13-1) as a template and the primers as shown by SEQ ID NO: 71 and SEQ ID NO: 75. The DNA fragment obtained via PCR was designated as (REPP3M)-phaJ4b. Subsequently, PCR was carried out under the same conditions as with (13-1) using REP-PU and (REPP3M)-phaJ4b as templates and the primers as shown by SEQ ID NO: 72 and SEQ ID NO: 71. The DNA fragment obtained via PCR was digested with EcoRI. This DNA fragment was designated as REPP3M-phaJ4b(EcoRI). REPP3M-phaJ4b (EcoRI) was ligated to the plasmid vector pCUP2 disclosed in WO 2007/049716, which had been cleaved MunI. The nucleotide sequence of the plasmid vector comprising REPP3M-phaJ4b(EcoRI) ligated to pCUP2, which had been cleaved with MunI, was determined in the same manner as in (13-1), the plasmid resulting from the introduction of a mutation into the plasmid vector pCUP2-REP-phaJ4b prepared in (13-1) at the nucleotide sequence of the phaC1 promoter region as shown by SEQ ID NO: 73 was obtained and was designated as pCUP2-REPP3M14-phaJ4b.

(13-3) Preparation of the Promoter-Modified Plasmid Vector pCUP2-REPN17-phaJ4b

A mutation as shown by SEQ ID NO: 76 was introduced into the plasmid vector pCUP2-REP-phaJ4b prepared in (13-1) at the phaC1 promoter of the *C. necator* H16 strain that regulates phaJ4b expression, so as to prepare pCUP2-REPN17-phaJ4b in the manner described above.

PCR was carried out under the same conditions as with (13-1) using the plasmid vector pCUP2-REP-phaJ4b prepared in (1) above as a template and the primers as shown by SEQ ID NO: 71 and SEQ ID NO: 77. The DNA fragment obtained via PCR was designated as (REPN17)-phaJ4b. Subsequently, PCR was carried out under the same conditions as with (13-1) using REP-PU and (REPN17)-phaJ4b prepared in (13-2) as templates and the primers as shown by SEQ ID NO: 72 and SEQ ID NO: 71. The DNA fragment obtained via PCR was digested with EcoRI. This DNA fragment was designated as REPN17-phaJ4b(EcoRI). REPN17-phaJ4b(EcoRI) was ligated to the plasmid vector pCUP2 disclosed in WO 2007/049716, which had been cleaved with MunI. The nucleotide sequence of the plasmid vector comprising REPN17-phaJ4b(EcoRI) ligated to pCUP2, which had been cleaved with MunI, was determined in the same manner as in (13-1), the plasmid resulting from the introduction of a mutation into the pCUP2-REP-phaJ4b plasmid vector prepared in (13-1) at the nucleotide sequence of the phaC1 promoter region as shown by SEQ ID NO: 76 was obtained and was designated as pCUP2-REPN17-phaJ4b.

(13-4) Preparation of the SD Sequence-Modified Plasmid Vector pCUP2-REPSDM4-phaJ4b The phaC1 SD sequence of the *C. necator* H16 strain that regulates phaJ4b expression in the pCUP2-REP-phaJ4b plasmid vector prepared in (13-1) was modified into the nucleotide sequence (TGTGTGA: SEQ ID NO: 63), so as to prepare pCUP2-REPSDM4-phaJ4b in the manner described below.

PCR was carried out under the same conditions as with (13-1) using the plasmid vector pCUP2-REP-phaJ4b prepared in (13-1) as a template and the primers as shown by SEQ ID NO: 71 and SEQ ID NO: 78. The DNA fragment obtained via PCR was designated as (REP)SDM4-phaJ4b. Subsequently, PCR was carried out under the same conditions as with (13-1) using the plasmid vector pCUP2-REP-phaJ4b prepared in (13-1) as a template and the primers as shown by SEQ ID NO: 72 and SEQ ID NO: 79. The DNA fragment obtained via PCR was designated as REP-SDU. Subsequently, PCR was carried out under the same conditions as with (13-1) using (REP)SDM4-phaJ4b and REP-SDU as templates and the primers as shown by SEQ ID NO: 72 and SEQ ID NO: 71. The DNA fragment obtained via PCR was digested with EcoRI. This DNA fragment was designated as REPSDM4-phaJ4b(EcoRI). REPSDM4-phaJ4b(EcoRI) was ligated to the pCUP2 plasmid vector disclosed in WO 2007/049716, which had been cleaved with MunI. The nucleotide sequence of the plasmid vector comprising REPSDM4-phaJ4b(EcoRI) ligated to pCUP2, which had been cleaved with MunI, was determined in the same manner as in (13-1), a plasmid derived from the plasmid vector pCUP2-REP-phaJ4b prepared in (13-1) via modification of the nucleotide sequence in the phaC1 SD sequence into TGTGTGA (SEQ ID NO: 63) was obtained, and such sequence was designated as pCUP2-REPSDM4-phaJ4b.

(13-5) Preparation of the SD Sequence-Modified Plasmid Vector pCUP2-REPSDM11-phaJ4b The phaC1 SD sequence of the *C. necator* H16 strain that regulates phaJ4b expression in the plasmid vector pCUP2-REP-phaJ4b prepared in (13-1) was modified into the nucleotide sequence (TCTCTCT: SEQ ID NO: 52), so as to prepare pCUP2-REPSDM11-phaJ4b in the manner described below.

PCR was carried out under the same conditions as with (13-1) using the plasmid vector pCUP2-REP-phaJ4b prepared in (13-1) as a template and the primers as shown by SEQ ID NO: 71 and SEQ ID NO: 80. The DNA fragment obtained via PCR was designated as (REP)SDM11-phaJ4b. Subsequently, PCR was carried out under the same conditions as with (13-1) using (REP)SDM11-phaJ4b and REP-SDU prepared in (13-4) as templates and the primers as shown by SEQ ID NO: 72 and SEQ ID NO: 71. The DNA fragment obtained via PCR was digested with EcoRI. This DNA fragment was designated as REPSDM11-phaJ4b (EcoRI). REPSDM11-phaJ4b(EcoRI) was ligated to the plasmid vector pCUP2 disclosed in WO 2007/049716, which had been cleaved with MunI.

The nucleotide sequence of the plasmid vector comprising REPSDM11-phaJ4b(EcoRI) ligated to pCUP2, which had been cleaved with MunI, was determined in the same manner as in (13-1), a plasmid derived from the plasmid vector pCUP2-REP-phaJ4b prepared in (13-1) via modification of the nucleotide sequence in the phaC1 SD sequence into TCTCTCT (SEQ ID NO: 52) was obtained and was designated as pCUP2-REPSDM11-phaJ4b.

(13-6) Preparation of the Plasmid Vector pCUP2-trcSDM1-phaJ4b (1) A plasmid vector pCUP2-trc-phaJ4b into which DNA comprising the trc promoter as shown by SEQ ID NO: 47, the phaC1 SD sequence of the *C. necator* H16 strain, and a nucleotide sequence comprising the phaJ4b gene has been inserted was prepared in the manner described below.

PCR was carried out under the same conditions as with (13-1) using the chromosome DNA of the *C. necator* H16 strain as a template and the primers as shown by SEQ ID NO: 81 and SEQ ID NO: 82. The DNA fragment obtained via PCR was digested with MunI and SpeI. This DNA fragment was designated as (ReSD)-phaJ4b(MunI, SpeI). (ReSD)-phaJ4b(MunI, SpeI) was ligated to the plasmid vector pCUP2 disclosed in WO 2007/049716, which had been cleaved MunI and SpeI. The nucleotide sequence of the plasmid vector comprising (ReSD)-phaJ4b(MunI, SpeI) ligated to pCUP2, which had been cleaved with MunI and SpeI, was determined in the same manner as in (13-1), and this nucleotide sequence was determined to be identical to the nucleotide sequence of the template DNA. The resulting plasmid was designated as pCUP2-ReSD-phaJ4b. Subsequently, PCR was carried out under the same conditions as with (13-1) using the pKK388-1 plasmid (manufactured by Clontech Laboratories, Inc.) as a template and the primers as shown by SEQ ID NO: 83 and SEQ ID NO: 85. The DNA fragment obtained via PCR was digested with MunI. This DNA fragment was designated as trc(MunI). Subsequently, trc(MunI) was ligated to the plasmid pCUP2-ReSD-phaJ4b, which had been cleaved with MunI. The nucleotide sequence of the plasmid vector comprising trc(MunI) ligated to pCUP2-ReSD-phaJ4b, which had been cleaved with MunI, was determined in the same manner as in (13-1), and this nucleotide sequence was determined to be identical to the nucleotide sequence of the template DNA. In addition, a plasmid comprising a trc(MunI) fragment inserted in such a direction that an amplified fragment comprising the trc promoter and the nucleotide sequence comprising the phaJ4b gene could be obtained when conducting PCR under the same conditions as with (13-1) using the plasmid vector as a template and the primers as shown by SEQ ID NO: 81 and SEQ ID NO: 83 was obtained. The resulting plasmid was designated as pCUP2-trc-phaJ4b.

(2) The phaC1 SD sequence of the *C. necator* H16 strain that regulates phaJ4b expression for the plasmid vector obtained above (pCUP2-trc-phaJ40b) was modified into the nucleotide sequence TGTGAGA (SEQ ID NO: 60), so as to prepare pCUP2-trcSDM1-phaJ4b in the manner described below.

PCR was carried out under the same conditions as with (13-1) using the chromosome DNA of the *C. necator* H16 strain as a template and the primers as shown by SEQ ID NO: 81 and SEQ ID NO: 84. The DNA fragment obtained via PCR was digested with SpeI, and the 5' terminus was phosphorylated with T4 polynucleotide kinase. This DNA fragment was designated as SDMA-phaJ4b(SpeI).

Subsequently, SDMA-phaJ4b(SpeI) was ligated to the plasmid pCUP2-trc-phaJ4b obtained in (13-6) (1), which had been cleaved with PmaCI and SpeI. The nucleotide sequence of the plasmid vector comprising SDMA-phaJ4b (SpeI) ligated to pCUP2-trc-phaJ4b, which had been cleaved with PmaCI and SpeI, was determined in the same manner as in (13-1), a plasmid in which the nucleotide sequence of the phaC1 SD sequence of the plasmid vector pCUP2-trc-phaJ4b prepared in (13-6) (1) had been modified into TGTGAGA (SEQ ID NO: 60) was obtained, and such sequence was designated as pCUP2-trcSDM11-phaJ4b.

(13-7) Preparation of the Plasmid Vector pCUP2-trcSDM3-phaJ4b

The nucleotide sequence of the phaC1 SD sequence of the *C. necator* H16 strain that regulates phaJ4b expression for the plasmid vector pCUP2-trc-phaJ4b prepared in (13-6) (1) was modified into AGTGAGA (SEQ ID NO: 62), so as to prepare pCUP2-trcSDM3-phaJ4b in the manner described below.

The nucleotide sequence of the plasmid vector comprising SDMA-phaJ4b(SpeI) ligated to pCUP2-trc-phaJ4b, which had been cleaved with PmaCI and SpeI, obtained by the method described in (13-6) (2) was determined in the same manner as in (13-1), the nucleotide sequence of the phaC1 SD sequence in the plasmid vector pCUP2-trc-phaJ4b prepared in (13-6) (1) was modified into AGTGAGA (SEQ ID NO: 62), and the resultant was designated as pCUP2-trcSDM3-phaJ4b.

(13-8) Preparation of the Plasmid Vector pCUP2-trcSDM4-phaJ4b

The phaC1 SD sequence of the *C. necator* H16 strain that regulates phaJ4b expression for the plasmid vector pCUP2-trc-phaJ4b prepared in (13-6) (1) was modified into the nucleotide sequence TGTGTGA (SEQ ID NO: 63), so as to prepare pCUP2-trcSDM4-phaJ4b in the manner described below.

The nucleotide sequence of the plasmid vector comprising SDMA-phaJ4b(SpeI) ligated to pCUP2-trc-phaJ4b, which had been cleaved with PmaCI and SpeI, obtained by the method described in (13-6) (2) was determined in the same manner as in (13-1), the nucleotide sequence of the phaC1 SD sequence in the plasmid vector pCUP2-trc-phaJ4b prepared in (13-6) (1) was modified into TGTGTGA (SEQ ID NO: 63), and the resultant was designated as pCUP2-trcSDM4-phaJ4b.

(13-9) Preparation of the Plasmid Vector pCUP2-trcSDM5-phaJ4b

The phaC1 SD sequence of the *C. necator* H16 strain that regulates phaJ4b expression in the plasmid vector pCUP2-trc-phaJ4b prepared in (13-6) (1) was modified into the nucleotide sequence TGAGTGA (SEQ ID NO: 64), so as to prepare pCUP2-trcSDM5-phaJ4b in the manner described below.

The nucleotide sequence of the plasmid vector comprising SDMA-phaJ4b(SpeI) ligated to pCUP2-trc-phaJ4b, which had been cleaved with PmaCI and SpeI, obtained by the method described in (13-6) (2) was determined in the same manner as in (13-1), the nucleotide sequence of the phaC1 SD sequence for the plasmid vector pCUP2-trc-phaJ4b prepared in (13-6) (1) was modified into TGAGTGA (SEQ ID NO: 64), and the resultant was designated as pCUP2-trcSDM5-phaJ4b.

(13-10) Preparation of the Plasmid Vector pCUP2-trc-SDM2-phaJ4b

The phaC1 SD sequence of the *C. necator* H16 strain that regulates phaJ4b expression in the plasmid vector pCUP2-trc-phaJ4b prepared in (13-6) (1) was modified into the nucleotide sequence ATATAGA (SEQ ID NO: 61), so as to prepare pCUP2-trcSDM2-phaJ4b in the manner described below.

PCR was carried out under the same conditions as with (13-1) using the chromosome DNA of the *C. necator* 1-116 strain as a template and the primers as shown by SEQ ID NO: 86 and SEQ ID NO: 81. The DNA fragment obtained via PCR was digested with SpeI, and the 5' terminus was phosphorylated with 14 polynucleotide kinase. This DNA fragment was designated as SDMG-phaJ4b(SpeI).

Subsequently, SDMG-phaJ4b(SpeI) was ligated to the plasmid pCUP2-trc-phaJ4b obtained in (13-6) (1), which had been cleaved with PmaCI and SpeI.

The nucleotide sequence of the plasmid vector comprising SDMG-phaJ4b(SpeI) ligated to pCUP2-trc-phaJ14b, which had been cleaved with PmaCI and SpeI, was determined in the same manner as in (13-1), the nucleotide sequence of the phaC1 SD sequence for the plasmid vector pCUP2-trc-phaJ4b prepared in (13-6) (1) was modified into ATATAGA (SEQ ID NO: 61), and the resultant was designated as pCUP2-trcSDM2-phaJ4b.

(13-11) Preparation of the Plasmid Vector pCUP2-trcSDM6-phaJ4b

The phaC1 SD sequence of the *C. necator* H16 strain that regulates phaJ4b expression for the plasmid vector pCUP2-trc-phaJ4b prepared in (13-6) (1) was modified into the nucleotide sequence AGAGATA (SEQ ID NO: 65), so as to prepare pCUP2-trcSDM6-phaJ4b in the manner described below.

The nucleotide sequence of the plasmid vector comprising SDMG-phaJ4b (SpeI) ligated to pCUP2-trc-phaJ4b, which had been cleaved with PmaCI and SpeI, obtained by the method described in (13-9) was determined in the same manner as in (13-1), the nucleotide sequence of the phaC1 SD sequence in the plasmid vector pCUP2-trc-phaJ4b prepared in (13-6) (1) was modified into AGAGATA (SEQ ID NO: 65), and the resultant was designated as pCUP2-trcSDM6-phaJ4b.

(13-12) Preparation of the Plasmid Vector pCUP2-trc-SDM7-phaJ4b

The phaC1 SD sequence of the *C. necator* H16 strain that regulates phaJ4b expression for the plasmid vector pCUP2-trc-phaJ4b prepared in (13-6) (1) was modified into the nucleotide sequence AGATAGA (SEQ ID NO: 66), so as to prepare pCUP2-trcSDM7-phaJ4b in the manner described below.

The nucleotide sequence of the plasmid vector comprising SDMG-phaJ4b (SpeI) ligated to pCUP2-trc-phaJ4b, which had been cleaved with PmaCI and SpeI, obtained by the method described in (13-9) was determined in the same manner as in (13-1), the nucleotide sequence of the phaC1 SD sequence for the plasmid vector pCUP2-trc-phaJ4b prepared in (13-6) (1) was modified into AGATAGA (SEQ ID NO: 66), and the resultant was designated as pCUP2-trcSDM7-phaJ4b.

(13-13) Analysis of the Amount of PHA Production and the 3HH Composition Ratio

The seed culture medium was composed of 1 w/v % meat extract, 1 w/v % Bacto-Tryptone, 0.2 w/v % yeast extract, 0.9 w/v % $Na_2HPO_4.12H_2O$, and 0.15 w/v % $KH_2PO_4$.

When strains into which plasmid vectors had been introduced were to be cultured using the seed culture medium, kanamycin was added to a final concentration of 100 µg/ml therein.

The PHA production medium was composed of 1.1 w/v % $Na_2HPO_4.12H_2O$, 0.19 w/v % $KH_2PO_4$, 0.13 w/v % $(NH_4)_2SO_4$, 0.1 w/v % $MgSO_4.7H_2O$, and 0.1 v/v % trace metal salts solution (1.6 w/v % $FeCl_3.6H_2O$, 1 w/v % $CaCl_2.2H_2O$, 0.02 w/v % $CoCl_2.6H_2O$, 0.016 w/v % $CuSO_4.5H_2O$, and 0.012 w/v % $NiCl_2.6H_2O$ dissolved in 0.1 N hydrochloric acid). Palm kernel olein, which is a low-melting fraction separated from palm kernel oil, was used as a single carbon source.

Glycerol stocks of 10 strains comprising the plasmid vectors introduced thereinto, which were obtained via transformation of the KNK005Δpha Z1,2,6 strain with the plasmid vectors prepared above; i.e., the pCUP2-REPN17-phaJ4b in KNK005Δpha Z1,2,6 strain, the pCUP2-REPSDM4-phaJ4b in KNK005Δpha Z1,2,6 the strain, the pCUP2-REPSDM11-phaJ4b in KNK005Δpha Z1,2,6 strain, the pCUP2-trcSDM1-phaJ4b in KNK005Δpha Z1,2,6 strain, the pCUP2-trcSDM3-phaJ4b in KNK005Δpha Z1,2,6 strain, the pCUP2-trcSDM4-phaJ4b in KNK005Δpha Z1,2,6 strain, the pCUP2-trcSDM5-phaJ4b in KNK005Δpha Z1,2,6 strain, the pCUP2-trcSDM2-phaJ4b in KNK005Δpha Z1,2,6 strain, the pCUP2-trcSDM6-phaJ4b in KNK005Δpha Z1,2,6 strain, and the pCUP2-trcSDM7-phaJ4b in KNK005Δpha Z1,2,6 strain, were prepared, 50 µl each of the glycerol stocks was inoculated into 10 ml each of the seed culture medium, and shake culture was conducted at 30° C. for 24 hours to obtain seed culture liquid.

At the time of culture for PHA production, the seed culture liquid was inoculated at 1.0 v/v % into a Sakaguchi flask containing 50 ml of the production medium. Shake culture was conducted at 30° C. for 72 hours. After the completion of culture, cells were recovered via centrifugation, washed with methanol, and freeze-dried. The weight of dry cells was then measured.

Chloroform (100 ml) was added to 1 g of the dry cells thus obtained, the mixture was stirred at room temperature during whole day and night, and PHAs were then extracted from the cells. After the residue of the cells was separated via filtration, the extract was concentrated to bring the total volume to 30 ml with an evaporator, 90 ml hexane was gradually added, and the mixture was then allowed to stand for 1 hour with slow stirring. The precipitated PHA was separated via filtration and then vacuum dried at 50° C. for 3 hours. The weight of the dry PHA was measured, and the amount of PHA produced was determined. The results are shown in Table 2.

The 3HH composition ratio of the produced polyesters was analyzed via gas chromatography in the manner described below. 2 ml of sulfuric acid-methanol (15:85) mixture and 2 ml of chloroform were added to about 20 mg of dry polyester. The system as tightly stoppered and heated at 100° C. for 140 minutes to afford methyl esters of the polyester degradation products. After cooling, 1.5 g of sodium bicarbonate was gradually added to neutralize the mixture, and the resultant was allowed to stand until generation of carbon dioxide gas ceased. Diisopropyl ether (4 ml) was added thereto, and the mixture was thoroughly mixed, followed by centrifugation. The monomer unit composition of the polyester degradation products in the supernatant was analyzed by capillary gas chromatography.

Capillary gas chromatography was performed using the gas chromatograph (GC-17A, manufactured by Shimadzu Corporation) and the capillary column (NEUTRA BOND-1, manufactured by GL Sciences Inc., column length: 25 m; column internal diameter: 0.25 mm, liquid film thickness: 0.4 µm). He carrier gas was used, a column inlet pressure was 100 kPa, and 1 µl of the sample was injected thereinto. The temperature conditions involved: an initial temperature of 100° C.; temperature elevation from 100° C. to 200° C. at a rate of 8° C./min; and additional temperature elevation from 200° C. to 290° C. at a rate of 30° C./min.

As a result of analysis conducted under the aforementioned conditions, the polyester obtained was found to be a polyester copolymer (i.e., P(3HB-co-3HH)), and the 3HH composition ratio was shown in Table 2.

TABLE 2

| Strain | Amount of PHA production (g/l) | 3HH composition ratio (mol %) |
|---|---|---|
| pCUP2-REPN17-phaJ4b in KNK005ΔphaZ1,2,6 | 16.2 | 6.68 |
| pCUP2-REPSDM4-phaJ4b in KNK005ΔphaZ1,2,6 | 16.9 | 6.61 |
| pCUP2-REPSDM11-phaJ4b in KNK005ΔphaZ1,2,6 | 16.5 | 6.60 |
| pCUP2-trcSDM1-phaJ4b in KNK005ΔphaZ1,2,6 | 16.1 | 10.25 |
| pCUP2-trcSDM3-phaJ4b in KNK005ΔphaZ1,2,6 | 16.5 | 10.36 |
| pCUP2-trcSDM4-phaJ4b in KNK005ΔphaZ1,2,6 | 17.3 | 9.44 |
| pCUP2-trcSDM5-phaJ4b in KNK005ΔphaZ1,2,6 | 16.7 | 10.07 |
| pCUP2-trcSDM2-phaJ4b in KNK005ΔphaZ1,2,6 | 15.8 | 10.42 |
| pCUP2-trcSDM6-phaJ4b in KNK005ΔphaZ1,2,6 | 17.7 | 10.00 |
| pCUP2-trcSDM7-phaJ4b in KNK005ΔphaZ1,2,6 | 18.2 | 10.36 |

INDUSTRIAL APPLICABILITY

The microorganisms according to the present invention enable the production of a polyhydroxyalkanoate (PHA) copolymer with a regulated monomer composition ratio. Thus, biodegradable polymers with an extensive range of physical properties from hard polymers to soft polymers can be produced.

All publications, patents, and patent applications cited herein are incorporated herein by reference in their entirety.

SEQUENCE LISTING FREE TEXT

SEQ ID NOs: 1 to 36, 70 to 72, 74 to 75, and 77 to 86: Primers

SEQ ID NOs: 38 to 40 and 43 to 45: Expression regulatory DNAs

SEQ ID NOs: 60 to 66: SD sequences

SEQ ID NOs: 76 and 55 to 59: Promoters

The invention claimed is:

1. A method for producing a polyhydroxyalkanoate (PHA) copolymer having at least 5 mol % of 3-hydroxyhexanoate (3HH) monomer, the method comprising:
culturing a microorganism comprising a (R)-specific enoyl-CoA hydratase gene in the genome DNA, wherein a nucleotide sequence upstream of the (R)-specific enoyl-CoA hydratase gene in the genome DNA of the microorganism comprises a modification that comprises a substitution, a deletion, an insertion, and/or an addition of at least one nucleotide so that expression of the (R)-specific enoyl-CoA hydratase gene is regulated, and further comprising a polyhydroxyalkanoate synthase gene, wherein the modification comprises a modification of at least one nucleotide in a promoter sequence and/or a Shine-Dalgarno (SD) sequence originally existing upstream of the (R)-specific enoyl-CoA hydratase gene in the genome DNA; or an insertion or substitution of an expression regulatory DNA comprising a promoter sequence and/or SD sequence, at a site upstream of the (R)-specific enoyl-CoA hydratase gene in the genome DNA, so that the mol % of the 3HH monomer is higher than a control without the modification;

wherein the modification comprises an insertion or substitution of an *E. coli*-derived promoter sequence selected from the group consisting of a trc promoter sequence, a lacUV5 promoter sequence, and a trp promoter sequence; and recovering a polyhydroxyalkanoate copolymer from the microorganism.

2. The method of claim 1, wherein the polyhydroxyalkanoate copolymer comprises, as a constitutive unit, from 8 to 13 mol % of 3-hydroxyhexanoic acid (3HH) monomer.

3. The method of claim 2, wherein the polyhydroxyalkanoate copolymer is a poly(3-hydroxybutyrate-co-3-hydroxyhexanoate.

4. The method of claim 1, wherein the insertion or substitution is at a position within 10,000 nucleotides upstream of the (R)-specific enoyl-CoA hydratase gene.

5. The method of claim 1, wherein the polyhydroxyalkanoate synthase gene is from *Aeromonas caviae*.

6. The method of claim 1, wherein the microorganism belongs to the genus *Cupriavidus*.

7. The method of claim 6, wherein the microorganism is *Cupriavidus necator*.

8. The method of claim 1, wherein the microorganism belongs to the genus *Aeromonas*.

9. The method of claim 8, wherein the microorganism is *Aeromonas hydrophila*.

10. The method of claim 1, wherein the (R)-specific enoyl-CoA hydratase gene forms an operon with another gene.

11. The method of claim 1, wherein the expression regulatory DNA further comprises a Shine-Dalgarno (SD) sequence of the phaC1 gene or a modified SD sequence thereof, wherein the SD sequence or modified SD sequence comprises a nucleotide sequence selected from the group consisting of the nucleotide sequences of SEQ ID NOs: 51, 52, and 60 to 66.

12. The method of claim 1, wherein the microorganism comprises an expression regulatory DNA, which comprises a promoter comprising a nucleotide sequence selected from the group consisting of the nucleotide sequences of SEQ ID NOs: 47, 48, and 50 and an SD sequence comprising a nucleotide sequence selected from the group consisting of the nucleotide sequences of SEQ ID NOs: 51, 52, and 60 to 66.

13. The method of claim 1, wherein the microorganism comprises an expression regulatory DNA comprising a nucleotide sequence selected from the group consisting nucleotide sequences of SEQ ID NOs: 38-40 and 43-45.

14. The method of claim 1, wherein the trc promoter sequence comprises the nucleotide sequence of SEQ ID NO: 47.

15. The method of claim 1, wherein the trp promoter sequence comprises the nucleotide sequence of SEQ ID NO: 48.

16. The method of claim 1, wherein the lacUV5 promoter sequence comprises the nucleotide sequence of SEQ ID NO: 50.

* * * * *

SEQUENCE LISTING

<160> NUMBER OF SEQ ID NOS: 86

<210> SEQ ID NO 1
<211> LENGTH: 32
<212> TYPE: DNA
<213> ORGANISM: Artificial
<220> FEATURE:
<223> OTHER INFORMATION: primer

<400> SEQUENCE: 1
gcgcatttaa atccggacct tcgtgcggct ca          32

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
gaggactcct gatcgtgtga          20

<210> SEQ ID NO 3
<211> LENGTH: 40
<212> TYPE: DNA
<213> ORGANISM: Artificial
<220> FEATURE:
<223> OTHER INFORMATION: primer

<400> SEQUENCE: 3
tcacacgatc aggagtcctc agtcgggcag caccaatgcg          40

<210> SEQ ID NO 4
<211> LENGTH: 32
<212> TYPE: DNA
<213> ORGANISM: Artificial
<220> FEATURE:
<223> OTHER INFORMATION: primer

<400> SEQUENCE: 4
gcgcatttaa atcgccacgc tgtgcctgac ga          32

<210> SEQ ID NO 5
<211> LENGTH: 34
<212> TYPE: DNA
<213> ORGANISM: Artificial
<220> FEATURE:
<223> OTHER INFORMATION: primer

<400> SEQUENCE: 5
gcgcgcattt aaatcatggc atctacgccg tcgg          34

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
gccttttctg cctgggtcta          20

<210> SEQ ID NO 7
<211> LENGTH: 40
<212> TYPE: DNA
<213> ORGANISM: Artificial

```
<220> FEATURE:
<223> OTHER INFORMATION: primer

<400> SEQUENCE: 7
tagacccagg cagaaaaggc gaaaacgccc gcgattgcgg                    40

<210> SEQ ID NO 8
<211> LENGTH: 34
<212> TYPE: DNA
<213> ORGANISM: Artificial
<220> FEATURE:
<223> OTHER INFORMATION: primer

<400> SEQUENCE: 8
gcgcgcattt aaatacgctg gcgcgtttcg tctg                          34

<210> SEQ ID NO 9
<211> LENGTH: 32
<212> TYPE: DNA
<213> ORGANISM: Artificial
<220> FEATURE:
<223> OTHER INFORMATION: primer

<400> SEQUENCE: 9
aaatagattt aaatgggaca gcagcaggat tt                            32

<210> SEQ ID NO 10
<211> LENGTH: 38
<212> TYPE: DNA
<213> ORGANISM: Artificial
<220> FEATURE:
<223> OTHER INFORMATION: primer

<400> SEQUENCE: 10
gctggcggct gccgggggct cggtccccgc tattctgg                      38

<210> SEQ ID NO 11
<211> LENGTH: 38
<212> TYPE: DNA
<213> ORGANISM: Artificial
<220> FEATURE:
<223> OTHER INFORMATION: primer

<400> SEQUENCE: 11
ccagaatagc ggggaccgag cccccggcag ccgccagc                      38

<210> SEQ ID NO 12
<211> LENGTH: 33
<212> TYPE: DNA
<213> ORGANISM: Artificial
<220> FEATURE:
<223> OTHER INFORMATION: primer

<400> SEQUENCE: 12
aaatagattt aaatacaaag gcaaagggt agc                            33

<210> SEQ ID NO 13
<211> LENGTH: 34
<212> TYPE: DNA
<213> ORGANISM: Artificial
<220> FEATURE:
<223> OTHER INFORMATION: primer

<400> SEQUENCE: 13
gcgcgcattt aaatgcaagc agttcggcgt ggcg                          34
```

<210> SEQ ID NO 14
<211> LENGTH: 25
<212> TYPE: DNA
<213> ORGANISM: Artificial
<220> FEATURE:
<223> OTHER INFORMATION: primer

<400> SEQUENCE: 14
gcttgctctt cctattcagt caggg                                       25

<210> SEQ ID NO 15
<211> LENGTH: 43
<212> TYPE: DNA
<213> ORGANISM: Artificial
<220> FEATURE:
<223> OTHER INFORMATION: primer

<400> SEQUENCE: 15
gcagagagac aatcaaatca tgaagaccta cgagaacatc gcc                   43

<210> SEQ ID NO 16
<211> LENGTH: 33
<212> TYPE: DNA
<213> ORGANISM: Artificial
<220> FEATURE:
<223> OTHER INFORMATION: primer

<400> SEQUENCE: 16
gcgcgcattt aaattcaggg aaagcgccgc agg                              33

<210> SEQ ID NO 17
<211> LENGTH: 45
<212> TYPE: DNA
<213> ORGANISM: Artificial
<220> FEATURE:
<223> OTHER INFORMATION: primer

<400> SEQUENCE: 17
ccctgactga ataggaagag caagctgctt ctggcgtcag gcagc                 45

<210> SEQ ID NO 18
<211> LENGTH: 55
<212> TYPE: DNA
<213> ORGANISM: Artificial
<220> FEATURE:
<223> OTHER INFORMATION: primer

<400> SEQUENCE: 18
gatttgattg tctctctgca cgtgcaattg tttcctgtgt gaaattgtta tccgc      55

<210> SEQ ID NO 19
<211> LENGTH: 51
<212> TYPE: DNA
<213> ORGANISM: Artificial
<220> FEATURE:
<223> OTHER INFORMATION: primer

<400> SEQUENCE: 19
ccctgactga ataggaagag caagcgcgca acgcaattaa tgtgagttag c          51

<210> SEQ ID NO 20
<211> LENGTH: 95
<212> TYPE: DNA
<213> ORGANISM: Artificial
<220> FEATURE:
<223> OTHER INFORMATION: primer

```
<400> SEQUENCE: 20
gatttgattg tctctctgca cgtgcaattg tttcctgtgt gaaattgtta tccgctcaca      60
attccacaca ttatacgagc cggaagcata aagtg                                 95

<210> SEQ ID NO 21
<211> LENGTH: 106
<212> TYPE: DNA
<213> ORGANISM: Artificial
<220> FEATURE:
<223> OTHER INFORMATION: primer

<400> SEQUENCE: 21
gatttgattg tctctctgca cgtgcaattg tttcctgtgt gaaattgtta tccgctgtga      60
acttgcgtac tagttaacta gttcgatgat taattgtcaa cagctc                    106

<210> SEQ ID NO 22
<211> LENGTH: 45
<212> TYPE: DNA
<213> ORGANISM: Artificial
<220> FEATURE:
<223> OTHER INFORMATION: primer

<400> SEQUENCE: 22
ccctgactga ataggaagag caagccccgg gcaagtacct tgccg                      45

<210> SEQ ID NO 23
<211> LENGTH: 22
<212> TYPE: DNA
<213> ORGANISM: Artificial
<220> FEATURE:
<223> OTHER INFORMATION: primer

<400> SEQUENCE: 23
catgatttga ttgtctctct gc                                               22

<210> SEQ ID NO 24
<211> LENGTH: 43
<212> TYPE: DNA
<213> ORGANISM: Artificial
<220> FEATURE:
<223> OTHER INFORMATION: primer

<400> SEQUENCE: 24
gctctctctc aatcaaatca tgaagaccta cgagaacatc gcc                        43

<210> SEQ ID NO 25
<211> LENGTH: 42
<212> TYPE: DNA
<213> ORGANISM: Artificial
<220> FEATURE:
<223> OTHER INFORMATION: primer

<400> SEQUENCE: 25
gatttgattg agagagagcc gtcactattc gaaccggctc cg                         42

<210> SEQ ID NO 26
<211> LENGTH: 30
<212> TYPE: DNA
<213> ORGANISM: Artificial
<220> FEATURE:
<223> OTHER INFORMATION: primer

<400> SEQUENCE: 26
```

```
tgcgggaatc cgcctcggca ctgcacgctt                                      30
```

<210> SEQ ID NO 27
<211> LENGTH: 73
<212> TYPE: DNA
<213> ORGANISM: Artificial
<220> FEATURE:
<223> OTHER INFORMATION: primer

<400> SEQUENCE: 27

```
gtgccgaggc ggattcccgc attgacagcg cgtgcttgca aggcaacaat ggactcaaat    60
gtctcggaat cgc                                                       73
```

<210> SEQ ID NO 28
<211> LENGTH: 38
<212> TYPE: DNA
<213> ORGANISM: Artificial
<220> FEATURE:
<223> OTHER INFORMATION: primer

<400> SEQUENCE: 28

```
gcgcgcattt aaatcgagga agagatcctg gcctttgc                             38
```

<210> SEQ ID NO 29
<211> LENGTH: 29
<212> TYPE: DNA
<213> ORGANISM: Artificial
<220> FEATURE:
<223> OTHER INFORMATION: primer

<400> SEQUENCE: 29

```
gtcgatagtc tcctcttgac gataaagtg                                       29
```

<210> SEQ ID NO 30
<211> LENGTH: 41
<212> TYPE: DNA
<213> ORGANISM: Artificial
<220> FEATURE:
<223> OTHER INFORMATION: primer

<400> SEQUENCE: 30

```
gctctctctc aatcaaatca tgcgtaccat cgcatcgctg g                         41
```

<210> SEQ ID NO 31
<211> LENGTH: 33
<212> TYPE: DNA
<213> ORGANISM: Artificial
<220> FEATURE:
<223> OTHER INFORMATION: primer

<400> SEQUENCE: 31

```
gcgcgcattt aaattcaccc gtagcggcgc gtg                                  33
```

<210> SEQ ID NO 32
<211> LENGTH: 49
<212> TYPE: DNA
<213> ORGANISM: Artificial
<220> FEATURE:
<223> OTHER INFORMATION: primer

<400> SEQUENCE: 32

```
cactttatcg tcaagaggag actatcgact gcttctggcg tcaggcagc                 49
```

<210> SEQ ID NO 33
<211> LENGTH: 45

<212> TYPE: DNA
<213> ORGANISM: Artificial
<220> FEATURE:
<223> OTHER INFORMATION: primer

<400> SEQUENCE: 33
catgatttga ttgagagaga gcacgtgcaa ttgtttcctg tgtga          45

<210> SEQ ID NO 34
<211> LENGTH: 41
<212> TYPE: DNA
<213> ORGANISM: Artificial
<220> FEATURE:
<223> OTHER INFORMATION: primer

<400> SEQUENCE: 34
gcagagagac aatcaaatca tgcgtaccat cgcatcgctg g               41

<210> SEQ ID NO 35
<211> LENGTH: 55
<212> TYPE: DNA
<213> ORGANISM: Artificial
<220> FEATURE:
<223> OTHER INFORMATION: primer

<400> SEQUENCE: 35
cactttatcg tcaagaggag actatcgacg cgcaacgcaa ttaatgtgag ttagc     55

<210> SEQ ID NO 36
<211> LENGTH: 49
<212> TYPE: DNA
<213> ORGANISM: Artificial
<220> FEATURE:
<223> OTHER INFORMATION: primer

<400> SEQUENCE: 36
cactttatcg tcaagaggag actatcgacc ccgggcaagt accttgccg        49

<210> SEQ ID NO 37
<211> LENGTH: 842
<212> TYPE: DNA
<213> ORGANISM: Cupriavidus necator

<400> SEQUENCE: 37
cccgggcaag taccttgccg acatctatgc gctggcgcgc acgcgcctgg cgcgcgccgg    60
ctgtaccgag gtctacggcg gcgacgcctg caccgtggcc gacgccggtc gcttctactc    120
ctatcggcgc gatggcgtga ccggccgcat ggccagcctg gtctggctgg cggactgagc    180
ccgccgctgc ctcactcgtc cttgcccctg gccgcctgcg cgcgctcggc ttcagccttg    240
cgtcggcggc ggccgggcgt gcccatgatg tagagcacca cgccaccgg cgccatgcca    300
tacatcagga aggtggcaac gcctgccacc acgttgtgct cggtgatcgc catcatcagc    360
gccacgtaga gccagccaat ggccacgatg tacatcaaaa attcatcctt ctcgcctatg    420
ctctggggcc tcggcagatg cgagcgctgc ataccgtccg gtaggtcggg aagcgtgcag    480
tgccgaggcg gattcccgca ttgacagcgc gtgcgttgca aggcaacaat ggactcaaat    540
gtctcggaat cgctgacgat tcccaggttt ctccggcaag catagcgcat ggcgtctcca    600
tgcgagaatg tcgcgcttgc cggataaaag gggagccgct atcggaatgg acgcaagcca    660
cggccgcagc aggtgcggtc gagggcttcc agccagttcc agggcagatg tgccggagga    720
ccctcccgct ttgggggagg cgcaagccgg gtccattcgg atagcatctc cccatgcaaa    780

```
gtgccggcca gggcaatgcc cggagccggt tcgaatagtg acggcagaga gacaatcaaa    840
tc                                                                  842

<210> SEQ ID NO 38
<211> LENGTH: 254
<212> TYPE: DNA
<213> ORGANISM: Artificial
<220> FEATURE:
<223> OTHER INFORMATION: expression-regulating DNA

<400> SEQUENCE: 38
tgcttctggc gtcaggcagc catcggaagc tgtggtatgg ctgtgcaggt cgtaaatcac     60
tgcataattc gtgtcgctca aggcgcactc ccgttctgga taatgttttt tgcgccgaca    120
tcataacggt tctggcaaat attctgaaat gagctgttga caattaatca tccggctcgt    180
ataatgtgtg gaattgtgag cggataacaa tttcacacag gaaacaattg cacgtgcaga    240
gagacaatca aatc                                                     254

<210> SEQ ID NO 39
<211> LENGTH: 147
<212> TYPE: DNA
<213> ORGANISM: Artificial
<220> FEATURE:
<223> OTHER INFORMATION: expression-regulating DNA

<400> SEQUENCE: 39
gcgcaacgca attaatgtga gttagctcac tcattaggca ccccaggctt tacactttat     60
gcttccggct cgtataatgt gtggaattgt gagcggataa caatttcaca caggaaacaa    120
ttgcacgtgc agagagacaa tcaaatc                                       147

<210> SEQ ID NO 40
<211> LENGTH: 256
<212> TYPE: DNA
<213> ORGANISM: Artificial
<220> FEATURE:
<223> OTHER INFORMATION: expression-regulating DNA

<400> SEQUENCE: 40
tgcttctggc gtcaggcagc catcggaagc tgtggtatgg ctgtgcaggt cgtaaatcac     60
tgcataattc gtgtcgctca aggcgcactc ccgttctgga taatgttttt tgcgccgaca    120
tcataacggt tctggcaaat attctgaaat gagctgttga caattaatca tcgaactagt    180
taactagtac gcaagttcac agcggataac aatttcacac aggaaacaat tgcacgtgca    240
gagagacaat caaatc                                                   256

<210> SEQ ID NO 41
<211> LENGTH: 842
<212> TYPE: DNA
<213> ORGANISM: Cupriavidus necator

<400> SEQUENCE: 41
cccgggcaag taccttgccg acatctatgc gctggcgcgc acgcgcctgg cgcgcgccgg     60
ctgtaccgag gtctacggcg gcgacgcctg caccgtggcc gacgccggtc gcttctactc    120
ctatcggcgc gatggcgtga ccggccgcat ggccagcctg gtctggctgg cggactgagc    180
ccgccgctgc ctcactcgtc cttgcccctg gccgcctgcg cgcgctcggc ttcagccttg    240
cgtcggcggc ggccgggcgt gcccatgatg tagagcacca cgccaccgg cgccatgcca    300 tacatcagga aggtggcaac gcctgccacc acgttgtgct cggtgatcgc catcatcagc    360
```

```
gccacgtaga gccagccaat ggccacgatg tacatcaaaa attcatcctt ctcgcctatg      420
ctctggggcc tcggcagatg cgagcgctgc ataccgtccg gtaggtcggg aagcgtgcag      480
tgccgaggcg gattcccgca ttgacagcgc gtgcgttgca aggcaacaat ggactcaaat      540
gtctcggaat cgctgacgat tcccaggttt ctccggcaag catagcgcat ggcgtctcca      600
tgcgagaatg tcgcgcttgc cggataaaag gggagccgct atcggaatgg acgcaagcca      660
cggccgcagc aggtgcggtc gagggcttcc agccagttcc agggcagatg tgccggcaga      720
ccctcccgct ttgggggagg cgcaagccgg gtccattcgg atagcatctc cccatgcaaa      780
gtgccggcca gggcaatgcc cggagccggt tcgaatagtg acggctctct ctcaatcaaa      840
tc                                                                    842

<210> SEQ ID NO 42
<211> LENGTH: 841
<212> TYPE: DNA
<213> ORGANISM: Cupriavidus necator

<400> SEQUENCE: 42
cccgggcaag taccttgccg acatctatgc gctggcgcgc acgcgcctgg cgcgcgccgg       60
ctgtaccgag gtctacggcg gcgacgcctg caccgtggcc gacgccggtc gcttctactc      120
ctatcggcgc gatggcgtga ccggccgcat ggccagcctg gtctggctgg cggactgagc      180
ccgccgctgc ctcactcgtc cttgcccctg gccgcctgcg cgcgctcggc ttcagccttg      240
cgtcggcggc ggccgggcgt gcccatgatg tagagcacca cgccaccgg cgccatgcca      300 tacatcagga aggtggcaac gcctgccacc acgttgtgct cggtgatcgc catcatcagc      360
gccacgtaga gccagccaat ggccacgatg tacatcaaaa attcatcctt ctcgcctatg      420
ctctggggcc tcggcagatg cgagcgctgc ataccgtccg gtaggtcggg aagcgtgcag      480
tgccgaggcg gattcccgca ttgacagcgc gtgcttgcaa ggcaacaatg gactcaaatg      540
tctcggaatc gctgacgatt cccaggtttc tccggcaagc atagcgcatg gcgtctccat      600
gcgagaatgt cgcgcttgcc ggataaaagg ggagccgcta tcggaatgga cgcaagccac      660
ggccgcagca ggtgcggtcg agggcttcca gccagttcca gggcagatgt gccggcagac      720
cctcccgctt tgggggaggc gcaagccggg tccattcgga tagcatctcc ccatgcaaag      780
tgccggccag ggcaatgccc ggagccggtt cgaatagtga cggctctctc tcaatcaaat      840
c                                                                     841

<210> SEQ ID NO 43
<211> LENGTH: 254
<212> TYPE: DNA
<213> ORGANISM: Artificial
<220> FEATURE:
<223> OTHER INFORMATION: expression-regulating DNA

<400> SEQUENCE: 43
tgcttctggc gtcaggcagc catcggaagc tgtggtatgg ctgtgcaggt cgtaaatcac       60
tgcataattc gtgtcgctca aggcgcactc ccgttctgga taatgttttt tgcgccgaca      120
tcataacggt tctggcaaat attctgaaat gagctgttga caattaatca tccggctcgt      180
ataatgtgtg gaattgtgag cggataacaa tttcacacag gaaacaattg cacgtgctct      240
ctctcaatca aatc                                                       254

<210> SEQ ID NO 44
```

```
<211> LENGTH: 147
<212> TYPE: DNA
<213> ORGANISM: Artificial
<220> FEATURE:
<223> OTHER INFORMATION: expression-regulating DNA

<400> SEQUENCE: 44
gcgcaacgca attaatgtga gttagctcac tcattaggca ccccaggctt tacactttat      60
gcttccggct cgtataatgt gtggaattgt gagcggataa caatttcaca caggaaacaa     120
ttgcacgtgc tctctctcaa tcaaatc                                         147

<210> SEQ ID NO 45
<211> LENGTH: 256
<212> TYPE: DNA
<213> ORGANISM: Artificial
<220> FEATURE:
<223> OTHER INFORMATION: expression-regulating DNA

<400> SEQUENCE: 45
tgcttctggc gtcaggcagc catcggaagc tgtggtatgg ctgtgcaggt cgtaaatcac      60
tgcataattc gtgtcgctca aggcgcactc ccgttctgga taatgttttt tgcgccgaca     120
tcataacggt tctggcaaat attctgaaat gagctgttga caattaatca tcgaactagt     180
taactagtac gcaagttcac agcggataac aatttcacac aggaaacaat tgcacgtgct     240
ctctctcaat caaatc                                                     256

<210> SEQ ID NO 46
<211> LENGTH: 594
<212> TYPE: PRT
<213> ORGANISM: Aeromonas caviae

<400> SEQUENCE: 46

Met Ser Gln Pro Ser Tyr Gly Pro Leu Phe Glu Ala Leu Ala His Tyr
1               5                   10                  15

Asn Asp Lys Leu Leu Ala Met Ala Lys Ala Gln Thr Glu Arg Thr Ala
            20                  25                  30

Gln Ala Leu Leu Gln Thr Asn Leu Asp Asp Leu Gly Gln Val Leu Glu
        35                  40                  45

Gln Gly Ser Gln Gln Pro Trp Gln Leu Ile Gln Ala Gln Met Asn Trp
    50                  55                  60

Trp Gln Asp Gln Leu Lys Leu Met Gln His Thr Leu Leu Lys Ser Ala
65                  70                  75                  80

Gly Gln Pro Ser Glu Pro Val Ile Thr Pro Glu Arg Ser Asp Arg Arg
                85                  90                  95

Phe Lys Ala Glu Ala Trp Ser Glu Gln Pro Ile Tyr Asp Tyr Leu Lys
            100                 105                 110

Gln Ser Tyr Leu Leu Thr Ala Arg His Leu Leu Ala Ser Val Asp Ala
        115                 120                 125

Leu Glu Gly Val Pro Gln Lys Ser Arg Glu Arg Leu Arg Phe Phe Thr
    130                 135                 140

Arg Gln Tyr Val Ser Ala Met Ala Pro Ser Asn Phe Leu Ala Thr Asn
145                 150                 155                 160

Pro Glu Leu Leu Lys Leu Thr Leu Glu Ser Gly Gly Gln Asn Leu Val
                165                 170                 175

Arg Gly Leu Ala Leu Leu Ala Glu Asp Leu Glu Arg Ser Ala Asp Gln
            180                 185                 190

Leu Asn Ile Arg Leu Thr Asp Glu Ser Ala Phe Glu Leu Gly Arg Asp
```

```
                    195                 200                 205
Leu Ala Leu Thr Pro Gly Arg Val Val Gln Arg Thr Glu Leu Tyr Glu
210                 215                 220

Leu Ile Gln Tyr Ser Pro Thr Thr Glu Thr Val Gly Lys Thr Pro Val
225                 230                 235                 240

Leu Ile Val Pro Pro Phe Ile Asn Lys Tyr Tyr Ile Met Asp Met Arg
                245                 250                 255

Pro Gln Asn Ser Leu Val Ala Trp Leu Val Ala Gln Gly Gln Thr Val
                260                 265                 270

Phe Met Ile Ser Trp Arg Asn Pro Gly Val Ala Gln Ala Gln Ile Asp
                275                 280                 285

Leu Asp Asp Tyr Val Val Asp Gly Val Ile Ala Ala Leu Asp Gly Val
290                 295                 300

Glu Ala Ala Thr Gly Glu Arg Glu Val His Gly Ile Gly Tyr Cys Ile
305                 310                 315                 320

Gly Gly Thr Ala Leu Ser Leu Ala Met Gly Trp Leu Ala Ala Arg Arg
                325                 330                 335

Gln Lys Gln Arg Val Arg Thr Ala Thr Leu Phe Thr Thr Leu Leu Asp
                340                 345                 350

Phe Ser Gln Pro Gly Glu Leu Gly Ile Phe Ile His Glu Pro Ile Ile
                355                 360                 365

Ala Ala Leu Glu Ala Gln Asn Glu Ala Lys Gly Ile Met Asp Gly Arg
370                 375                 380

Gln Leu Ala Val Ser Phe Ser Leu Leu Arg Glu Asn Ser Leu Tyr Trp
385                 390                 395                 400

Asn Tyr Tyr Ile Asp Ser Tyr Leu Lys Gly Gln Ser Pro Val Ala Phe
                405                 410                 415

Asp Leu Leu His Trp Asn Ser Asp Ser Thr Asn Val Ala Gly Lys Thr
                420                 425                 430

His Asn Ser Leu Leu Arg Arg Leu Tyr Leu Glu Asn Gln Leu Val Lys
                435                 440                 445

Gly Glu Leu Lys Ile Arg Asn Thr Arg Ile Asp Leu Gly Lys Val Lys
450                 455                 460

Thr Pro Val Leu Leu Val Ser Ala Val Asp Asp His Ile Ala Leu Trp
465                 470                 475                 480

Gln Gly Thr Trp Gln Gly Met Lys Leu Phe Gly Gly Glu Gln Arg Phe
                485                 490                 495

Leu Leu Ala Glu Ser Gly His Ile Ala Gly Ile Ile Asn Pro Pro Ala
                500                 505                 510

Ala Asn Lys Tyr Gly Phe Trp His Asn Gly Ala Glu Ala Glu Ser Pro
                515                 520                 525

Glu Ser Trp Leu Ala Gly Ala Thr His Gln Gly Gly Ser Trp Trp Pro
                530                 535                 540

Glu Met Met Gly Phe Ile Gln Asn Arg Asp Glu Gly Ser Glu Pro Val
545                 550                 555                 560

Pro Ala Arg Val Pro Glu Glu Gly Leu Ala Pro Ala Pro Gly His Tyr
                565                 570                 575

Val Lys Val Arg Leu Asn Pro Val Phe Ala Cys Pro Thr Glu Glu Asp
                580                 585                 590

Ala Ala

<210> SEQ ID NO 47
<211> LENGTH: 29
```

```
<212> TYPE: DNA
<213> ORGANISM: Escherichia coli

<400> SEQUENCE: 47
ttgacaatta atcatccggc tcgtataat                                    29

<210> SEQ ID NO 48
<211> LENGTH: 29
<212> TYPE: DNA
<213> ORGANISM: Escherichia coli

<400> SEQUENCE: 48
ttgacaatta atcatcgaac tagttaact                                    29

<210> SEQ ID NO 49
<211> LENGTH: 30
<212> TYPE: DNA
<213> ORGANISM: Escherichia coli

<400> SEQUENCE: 49
tttacacttt atgcttccgg ctcgtatgtt                                   30

<210> SEQ ID NO 50
<211> LENGTH: 30
<212> TYPE: DNA
<213> ORGANISM: Escherichia coli

<400> SEQUENCE: 50
tttacacttt atgcttccgg ctcgtataat                                   30

<210> SEQ ID NO 51
<211> LENGTH: 7
<212> TYPE: DNA
<213> ORGANISM: Cupriavidus necator

<400> SEQUENCE: 51 agagaga                                                            7

<210> SEQ ID NO 52
<211> LENGTH: 7
<212> TYPE: DNA
<213> ORGANISM: Artificial
<220> FEATURE:
<223> OTHER INFORMATION: SD sequence

<400> SEQUENCE: 52 tctctct                                                            7

<210> SEQ ID NO 53
<211> LENGTH: 6
<212> TYPE: DNA
<213> ORGANISM: Escherichia coli

<400> SEQUENCE: 53 ttgaca                                                             6

<210> SEQ ID NO 54
<211> LENGTH: 6
<212> TYPE: DNA
<213> ORGANISM: Escherichia coli

<400> SEQUENCE: 54 tataat                                                             6
```

<210> SEQ ID NO 55
<211> LENGTH: 30
<212> TYPE: DNA
<213> ORGANISM: Artificial
<220> FEATURE:
<223> OTHER INFORMATION: promoter

<400> SEQUENCE: 55
ttgatagcgc gtgcgttgca aggcaacaat                                            30

<210> SEQ ID NO 56
<211> LENGTH: 30
<212> TYPE: DNA
<213> ORGANISM: Artificial
<220> FEATURE:
<223> OTHER INFORMATION: promoter

<400> SEQUENCE: 56
aagacagcgc gtgcgttgca aggcaacaat                                            30

<210> SEQ ID NO 57
<211> LENGTH: 30
<212> TYPE: DNA
<213> ORGANISM: Artificial
<220> FEATURE:
<223> OTHER INFORMATION: promoter

<400> SEQUENCE: 57
ttttcagcgc gtgcgttgca aggcaacaac                                            30

<210> SEQ ID NO 58
<211> LENGTH: 30
<212> TYPE: DNA
<213> ORGANISM: Artificial
<220> FEATURE:
<223> OTHER INFORMATION: promoter

<400> SEQUENCE: 58
tttacagcgc gtgcgttgca aggcaccaac                                            30

<210> SEQ ID NO 59
<211> LENGTH: 29
<212> TYPE: DNA
<213> ORGANISM: Artificial
<220> FEATURE:
<223> OTHER INFORMATION: promoter

<400> SEQUENCE: 59
ttgacagcgc gtgcttgcaa ggcaacaat                                             29

<210> SEQ ID NO 60
<211> LENGTH: 7
<212> TYPE: DNA
<213> ORGANISM: Artificial
<220> FEATURE:
<223> OTHER INFORMATION: SD sequence

<400> SEQUENCE: 60 tgtgaga                                                                      7

<210> SEQ ID NO 61
<211> LENGTH: 7
<212> TYPE: DNA
<213> ORGANISM: Artificial
<220> FEATURE:
<223> OTHER INFORMATION: SD sequence

```
<400> SEQUENCE: 61 atataga                                                              7

<210> SEQ ID NO 62
<211> LENGTH: 7
<212> TYPE: DNA
<213> ORGANISM: Artificial
<220> FEATURE:
<223> OTHER INFORMATION: SD sequence

<400> SEQUENCE: 62 agtgaga                                                              7

<210> SEQ ID NO 63
<211> LENGTH: 7
<212> TYPE: DNA
<213> ORGANISM: Artificial
<220> FEATURE:
<223> OTHER INFORMATION: SD sequence

<400> SEQUENCE: 63 tgtgtga                                                              7

<210> SEQ ID NO 64
<211> LENGTH: 7
<212> TYPE: DNA
<213> ORGANISM: Artificial
<220> FEATURE:
<223> OTHER INFORMATION: SD sequence

<400> SEQUENCE: 64 tgagtga                                                              7

<210> SEQ ID NO 65
<211> LENGTH: 7
<212> TYPE: DNA
<213> ORGANISM: Artificial
<220> FEATURE:
<223> OTHER INFORMATION: SD sequence

<400> SEQUENCE: 65 agagata                                                              7

<210> SEQ ID NO 66
<211> LENGTH: 7
<212> TYPE: DNA
<213> ORGANISM: Artificial
<220> FEATURE:
<223> OTHER INFORMATION: SD sequence

<400> SEQUENCE: 66 agataga                                                              7

<210> SEQ ID NO 67
<211> LENGTH: 30
<212> TYPE: DNA
<213> ORGANISM: Cupriavidus necator

<400> SEQUENCE: 67
ttgacagcgc gtgcgttgca aggcaacaat                                    30

<210> SEQ ID NO 68
<211> LENGTH: 6
<212> TYPE: DNA
```

```
<213> ORGANISM: Cupriavidus necator

<400> SEQUENCE: 68 aacaat                                                                      6

<210> SEQ ID NO 69
<211> LENGTH: 7
<212> TYPE: DNA
<213> ORGANISM: Cupriavidus necator

<400> SEQUENCE: 69 agagaga                                                                     7

<210> SEQ ID NO 70
<211> LENGTH: 43
<212> TYPE: DNA
<213> ORGANISM: Artificial
<220> FEATURE:
<223> OTHER INFORMATION: primer

<400> SEQUENCE: 70
gcagagagac aatcaaatca tgaagaccta cgagaacatc gcc                             43

<210> SEQ ID NO 71
<211> LENGTH: 63
<212> TYPE: DNA
<213> ORGANISM: Artificial
<220> FEATURE:
<223> OTHER INFORMATION: primer

<400> SEQUENCE: 71
gcgcgcgaat tccggctgcc gactggttga accaggccgg caggtcaggg aaagcgccgc           60
agg                                                                        63

<210> SEQ ID NO 72
<211> LENGTH: 32
<212> TYPE: DNA
<213> ORGANISM: Artificial
<220> FEATURE:
<223> OTHER INFORMATION: primer

<400> SEQUENCE: 72
gcgcgcgaat tccccgggca agtaccttgc cg                                         32

<210> SEQ ID NO 73
<211> LENGTH: 30
<212> TYPE: DNA
<213> ORGANISM: Cupriavidus necator

<400> SEQUENCE: 73
tttatagcgc gtgcgttgca aggcaacaat                                            30

<210> SEQ ID NO 74
<211> LENGTH: 30
<212> TYPE: DNA
<213> ORGANISM: Artificial
<220> FEATURE:
<223> OTHER INFORMATION: primer

<400> SEQUENCE: 74
tgcgggaatc cgcctcggca ctgcacgctt                                            30

<210> SEQ ID NO 75
<211> LENGTH: 74
```

```
<212> TYPE: DNA
<213> ORGANISM: Artificial
<220> FEATURE:
<223> OTHER INFORMATION: primer

<400> SEQUENCE: 75
gtgccgaggc ggattcccgc awtkayagcg cgtgcgttgc aaggcaacaa tggactcaaa      60
tgtctcggaa tcgc                                                        74

<210> SEQ ID NO 76
<211> LENGTH: 29
<212> TYPE: DNA
<213> ORGANISM: Artificial
<220> FEATURE:
<223> OTHER INFORMATION: promoter

<400> SEQUENCE: 76
ttgacagcgc gtgcttgcaa ggcaacaat                                        29

<210> SEQ ID NO 77
<211> LENGTH: 73
<212> TYPE: DNA
<213> ORGANISM: Artificial
<220> FEATURE:
<223> OTHER INFORMATION: primer

<400> SEQUENCE: 77
gtgccgaggc ggattcccgc attgacagcg cgtgcttgca aggcaacaat ggactcaaat      60
gtctcggaat cgc                                                         73

<210> SEQ ID NO 78
<211> LENGTH: 62
<212> TYPE: DNA
<213> ORGANISM: Artificial
<220> FEATURE:
<223> OTHER INFORMATION: primer

<400> SEQUENCE: 78
gagccggttc gaatagtgac ggctgtgtga caatcaaatc atgaagacct acgagaacat      60
cg                                                                     62

<210> SEQ ID NO 79
<211> LENGTH: 23
<212> TYPE: DNA
<213> ORGANISM: Artificial
<220> FEATURE:
<223> OTHER INFORMATION: primer

<400> SEQUENCE: 79
gccgtcacta ttcgaaccgg ctc                                              23

<210> SEQ ID NO 80
<211> LENGTH: 62
<212> TYPE: DNA
<213> ORGANISM: Artificial
<220> FEATURE:
<223> OTHER INFORMATION: primer

<400> SEQUENCE: 80
gagccggttc gaatagtgac ggctctctct caatcaaatc atgaagacct acgagaacat      60
cg                                                                     62

<210> SEQ ID NO 81
```

```
<211> LENGTH: 63
<212> TYPE: DNA
<213> ORGANISM: Artificial
<220> FEATURE:
<223> OTHER INFORMATION: primer

<400> SEQUENCE: 81
gcgcgcacta gtcggctgcc gactggttga accaggccgg caggtcaggg aaagcgccgc        60
agg                                                                     63

<210> SEQ ID NO 82
<211> LENGTH: 60
<212> TYPE: DNA
<213> ORGANISM: Artificial
<220> FEATURE:
<223> OTHER INFORMATION: primer

<400> SEQUENCE: 82
gcgcgccaat tgcacgtgca gagagacaat caaatcatga agacctacga gaacatcgcc        60

<210> SEQ ID NO 83
<211> LENGTH: 29
<212> TYPE: DNA
<213> ORGANISM: Artificial
<220> FEATURE:
<223> OTHER INFORMATION: primer

<400> SEQUENCE: 83
gcgcgccaat tgtgcttctg gcgtcaggc                                          29

<210> SEQ ID NO 84
<211> LENGTH: 45
<212> TYPE: DNA
<213> ORGANISM: Artificial
<220> FEATURE:
<223> OTHER INFORMATION: primer

<400> SEQUENCE: 84
gtgcwgwgwg acaatcaaat catgaagacc tacgagaaca tcgcc                        45

<210> SEQ ID NO 85
<211> LENGTH: 35
<212> TYPE: DNA
<213> ORGANISM: Artificial
<220> FEATURE:
<223> OTHER INFORMATION: primer

<400> SEQUENCE: 85
gcgcgccaat tgtttcctgt gtgaaattgt tatcc                                   35

<210> SEQ ID NO 86
<211> LENGTH: 45
<212> TYPE: DNA
<213> ORGANISM: Artificial
<220> FEATURE:
<223> OTHER INFORMATION: primer

<400> SEQUENCE: 86
gtgcakakak acaatcaaat catgaagacc tacgagaaca tcgcc                        45
```